US009764162B1

(12) United States Patent
Willcut et al.

(10) Patent No.: US 9,764,162 B1
(45) Date of Patent: Sep. 19, 2017

(54) AUTOMATED, DATA-DRIVEN TREATMENT MANAGEMENT SYSTEM FOR ADAPTIVE RADIOTHERAPY WORKFLOWS

(71) Applicant: Elekta, Inc., Atlanta, GA (US)

(72) Inventors: Virgil Matthew Willcut, Kirkwood, MO (US); Richard Henry Stark, Los Altos, CA (US)

(73) Assignee: Elekta, Inc., Atlanta, GA (US)

( * ) Notice: Subject to any disclaimer, the term of this patent is extended or adjusted under 35 U.S.C. 154(b) by 248 days.

(21) Appl. No.: 14/524,757

(22) Filed: Oct. 27, 2014

Related U.S. Application Data

(60) Provisional application No. 61/896,522, filed on Oct. 28, 2013.

(51) Int. Cl.
*A61N 5/10* (2006.01)
*A61B 5/00* (2006.01)
(Continued)

(52) U.S. Cl.
CPC ............ *A61N 5/1071* (2013.01); *A61B 5/743* (2013.01); *A61B 6/5217* (2013.01);
(Continued)

(58) Field of Classification Search
CPC .. A61B 6/00; A61B 6/46; A61B 6/461; A61B 6/467; A61B 6/468; A61B 6/50; A61B 6/52; A61B 6/5211; A61B 6/5217; A61B 6/5294; A61B 6/54; A61B 5/00; A61B 5/0002; A61B 5/48; A61B 5/4836; A61B 5/4842; A61B 5/4848; A61B 5/74; A61B 5/742; A61B 5/7435; A61B 5/743; A61B 2576/00; A61N 5/00; A61N 5/10; A61N 5/103; A61N 5/1031; A61N 5/1048; A61N 5/1049; A61N 5/1064;
(Continued)

(56) References Cited

U.S. PATENT DOCUMENTS

2003/0076926 A1* 4/2003 Renner ................ A61N 5/1048
378/65
2007/0088573 A1* 4/2007 Ruchala ................ A61N 5/103
705/2
(Continued)

*Primary Examiner* — Anastasia Midkiff
(74) *Attorney, Agent, or Firm* — Schwegman Lundberg & Woessner, P.A.

(57) ABSTRACT

Systems and methods can include obtaining computerized physician intent data representing an initial patient care plan; creating a computerized workflow to include a course of multiple radiation therapy sessions; performing instructions on the oncology computer system to generate control parameters for a radiation therapy apparatus to provide the radiation treatment in accordance with the workflow during the course of sessions; obtaining computerized treatment data after initiating the course of sessions; processing the computerized treatment data, using the processor circuit, to determine an indication of delivery or effect of the radiation treatment during the course of sessions based on the initial patient care plan relative to the workflow; using the indication of delivery or effect of the radiation treatment to adapt the patient care plan; and managing the workflow for the patient using the adapted patient care plan as the patient proceeds through a course of sessions.

23 Claims, 22 Drawing Sheets

(51) Int. Cl.
*A61B 6/00* (2006.01)
*G06F 19/00* (2011.01)
*G06Q 50/24* (2012.01)
*G06T 7/00* (2017.01)

(52) U.S. Cl.
CPC .......... *A61B 6/5294* (2013.01); *A61N 5/1048* (2013.01); *A61N 5/1064* (2013.01); *G06F 19/30* (2013.01); *G06F 19/3431* (2013.01); *G06T 7/0012* (2013.01); *G06T 7/0014* (2013.01); *G06T 7/0016* (2013.01); A61B 5/4836 (2013.01); A61N 5/103 (2013.01); A61N 5/1075 (2013.01); A61N 2005/1041 (2013.01); A61N 2005/1072 (2013.01); A61N 2005/1074 (2013.01); G06Q 50/24 (2013.01)

(58) Field of Classification Search
CPC .. A61N 5/1065; A61N 5/1067–5/1069; A61N 5/107; A61N 5/1071; A61N 5/1075; A61N 2005/1032; A61N 2005/1034; A61N 2005/1035; A61N 2005/1041; A61N 2005/1054; A61N 2005/1055; A61N 2005/1058; A61N 2005/1059; A61N 2005/1061; A61N 2005/1062; A61N 2005/1072; A61N 2005/1074; A61N 2005/1076; G06F 19/00; G06F 19/30; G06F 19/321; G06F 19/322; G06F 19/324; G06F 19/325; G06F 19/34; G06F 19/3431; G06F 19/3481; G06F 19/3487; G06Q 10/00; G06Q 50/00; G06Q 50/22; G06Q 50/24; G06T 7/0012; G06T 7/0014; G06T 7/0016
See application file for complete search history.

(56) References Cited

U.S. PATENT DOCUMENTS

| | | | |
|---|---|---|---|
| 2009/0252292 A1* | 10/2009 | Simon | A61N 5/1071 378/65 |
| 2010/0054413 A1* | 3/2010 | Sobering | A61N 5/1031 378/65 |
| 2012/0232324 A1* | 9/2012 | Brusasco | A61N 5/1048 600/1 |
| 2012/0277570 A1* | 11/2012 | Todor | A61B 6/12 600/407 |
| 2013/0204067 A1* | 8/2013 | Nord | A61N 5/1038 600/1 |

* cited by examiner

PHYSICIAN INTENT (RX/CONSTRAINTS)

PHYSICIAN INTENT: MRS JONES                                    CAREPLAN NAME

FRACTIONATION _____
CTV DOSE _____
PTV DOSE _____                                   OPTIMIZATION
                                                   REQUIRED ☐Y ☐N
PTV MARGIN _____                                 REQUIRED ☐Y ☐N
PTV MIN _____  PTV MAX _____
VOLUME STATS _____

$OAR_1$ MAX DOSE _____  VOLUME_UNDER X % OF PTV _____
                          VOLUME_UNDER Y % OF PTV _____
$OAR_2$ MAX DOSE _____        .
                                .
$OAR_3$ MAX DOSE _____        .

BUILD DYNAMICALLY
                                                   FROM ABOVE AND
                                                   MODIFY RIGHT FROM
                                                   THE DIAGRAM

VISUAL REPRESENTATION OF PTVS BASED ON PRESCRIPTION

| CAREPLAN | SCHEDULE | PRESCRIPTION | CONSTRAINTS | IGRT | MOTION MGMT | ONLINE ADAPT'N | OFFLINE ADAPT'N |

FIG. 8

PHYSICIAN INTENT (IGRT/MOTION MGMNT)

| PHYSICIAN INTENT: MRS JONES | | | | | CAREPLAN NAME |
|---|---|---|---|---|---|

IMAGING BEFORE TREATMENT

REGISTRATION TOOL   RIGID ____   3D VOLUME ____   SEQUENCE (EXAM CARD) ____

VIRTUAL COUCH SHIFT   MANDATORY   DEFORMABLE ____

DOSE PREDICTION   YES ☐   NO ☐   ALLOWED ☐

QA PLAN CHECK   YES ☐   NO ☐   ALLOWED ☐

REOPTIMIZE   YES ☐   NO ☐   ALLOWED ☐

IMAGING DURING TREATMENT

1D NAVIGATOR ☐

2D SINGLE PLANE ☐   2 PLANES ☐   3 PLANES ☐   ORTHOGONAL ☐
                                                PARALLEL ☐
                                                EN FACE ☐

COMBINATION 1D AND 2D   YES ☐   NO ☐

GATING   YES ☐   NO ☐

TRACKING   YES ☐   NO ☐

| GATING WINDOW (SPATIAL) | PTV | ☐ |
|---|---|---|
| | PTV + 5 Rcm | ☐ |
| GATING WINDOW (TEMPORAL) | 0.5 SECONDS | |

| CAREPLAN | SCHEDULE | PRESCRIPTION | CONSTRAINTS | IGRT | MOTION MGMT | ONLINE ADAPTN | OFFLINE ADAPTN |

FIG. 9

INTENDED (REFERENCE) PLAN - ESTABLISH TRACKING WINDOW
CONFORMAL ARC LUNG (MODULATE ON GANTRY SPEED AND DOSE VALUE)

SHOW CTV/PTV ☐
SHOW OAR1 ☐
SHOW OAR2 ☐
TRACK CONTINUOUSLY ☐
TRACK WITHIN ____ OF OAR1
TRACK ON PHASE  ☒ 1  ☒ 2  ☒ 3  ☐ 4

GATE OFF PHASE ____  ____  ____

TRANSVERSE

SAGITAL
8-10 RESPIRATORY PHASES FROM 4D CT ON MR.
PLAY THRU EACH AND SHOW LEAF MOVEMENT IN EACH BIN.

CORONAL

EN FACE VIEW GATING ANGLE

AUTOMATED, DATA-DRIVEN TREATMENT MANAGEMENT SYSTEM FOR ADAPTIVE RADIOTHERAPY WORKFLOWS

CLAIM OF PRIORITY

This patent application claims the benefit of priority, under 35 U.S.C. Section 119(e), to U.S. Provisional Patent Application Ser. No. 61/896,522, entitled "AUTOMATED, DATA-DRIVEN TREATMENT MANAGEMENT SYSTEM FOR ADAPTIVE RADIOTHERAPY WORKFLOWS," filed on Oct. 28, 2013, which is hereby incorporated by reference herein in its entirety.

TECHNICAL FIELD

Embodiments of the present invention pertain generally to a computerized method for the planning and delivery of radiation to living tissue. In particular, the present invention pertains to a treatment management system that provides a computerized method for managing the delivery of a course of radiation therapy to a cancer patient.

Overview

Radiation therapy has been utilized to treat cancers and other ailments in mammalian (e.g., human and animal) tissue. Intensity Modulated Radiation Therapy (IMRT) is an advanced type of radiotherapy that can use beam shaping Multi-Leaf Collimators (MLCs) to deliberately modulate segments of the incident beam to produce a desired dose distribution to tumors or specific areas within a tumor. A high energy beam of ionizing radiation is directed from an external source towards a patient (the beam may be rotating, such as in "arc therapy"), to produce a collimated beam of radiation directed to a target site of a patient. The placement and dose of the radiation beam should be accurately controlled to ensure the tumor receives the prescribed radiation, and the placement of the beam should be such as to minimize damage to the surrounding healthy tissue. Therefore, IMRT can involve changing the shape, size and intensity of the radiation beam to ensure the delivery of the prescribed radiation dose as conformally as possible to the dimensions and location of the patient's tumor.

One device for the delivery of radiation to a patient is a linear accelerator. The linear accelerator is a machine that accelerates electrons to produce high-energy photon beam(s) of radiation, which can be controlled, shaped, modulated by the MLC and directed to a specific location, e.g., the tumor. More than one type of energy beam may be provided by the linear accelerator (e.g., a high energy beam and a low energy beam; a diagnostic energy and a therapeutic energy, and the like). These energies can be selectable, and the selected energy can be controlled on a periodic basis.

Sometimes, linear accelerators can modulate the beam of radiation. This may include a multi-leaf collimator (MLC), which is a device made up of many mobile "leaves," that shapes each individual beam of radiation to fit the shape of the area to be treated. The MLC can also reduce the intensity of radiation approaching a target in a particular direction to avoid critical structures in the path of a segment of the radiation beam called a beamlet by having the leaves remain (e.g., dwell) in a particular position for a longer or shorter length of time. The MLC, in one aspect, can determine the field size and shape of the radiation beam to avoid healthy tissue that may be adjacent to the tumor (e.g., the field size of a conventional two bank multi-leaf collimator is of the order of 40×40 cm$^2$; and the field size of a mini-collimator is of the order of 16×20 cm$^2$). In addition to the MLC, other aspects of the linear accelerator can contribute to the beam profile, such as for example, the physics, the energy level, and whether a flattening filter is utilized. It is desirable to ensure that the radiation dose to the areas outside the tumor be as low as possible, but also that the whole target area is treated adequately. For, if the tumor areas are treated inadequately, the likelihood of cancer recurrence is increased. Further, if non-treatment regions are irradiated, then healthy tissue may be damaged, which may result in greater side effects and longer recovery times for the patient after treatment.

At other times, multiple sources of radiation may be employed, for example, a high energy accelerator capable of creating a therapeutic beam and a lower energy X-ray tube for producing a diagnostic beam. In an example, both may be mounted on the same rotating gantry, separated by 90 degrees. Further, both may have an associated flat panel detector for portal images and diagnostic images. In an example, two low energy units may be mounted away from or off the gantry, each having its own detector system, such as to provide multiple angles of diagnostic images concurrently, in addition to the therapeutic source. In an example there may be multiple therapeutic sources.

Most therapeutic X-ray apparatuses include one or more filters for the X-ray radiation, such as flattening filters, wedges, or diagnostic X-ray filters. These can be matched to the energy distribution of the X-rays being filtered. In an example, a source of radiation may be paired with Magnetic Resonance Imaging (MRI).

In an example, one or more sources of external radiation may be from a radioisotope (e.g., Cobalt 60 or Cesium 137). In an example, a gamma knife system manufactured by Elekta, (Leksell Gamma Knife®, Elekta AB, Stockholm, Sweden) uses Cobalt 60. In an example, the external source of radiation may be from a particle accelerator (e.g., proton or carbon particle acceleration).

Furthermore, in an example, the source of radiation may be placed internal to the patient as in the case of Brachytherapy. These radiation sources may be placed permanently or they may be inserted temporarily into the patient. These sources may be either electronically produced or may take the form of a radioactive isotope that can be either sealed (e.g., Cobalt Co$^{60}$ for use in external beam radiation therapy) or unsealed source (e.g., orally administered iodine I$^{131}$ for the treatment of thyroid cancer).

As part of the radiation therapy process, a plurality of images can be obtained of the patient (e.g., CT imaging, X-ray images, radiotherapy portal images, magnetic resonance imaging (MRI) images, positron emission tomography (PET) images, single-photon emission computed tomography (SPECT) images, and the like). These images are stored in a memory (e.g., the memory may be local to the radiation therapy system or may be remote), which may be accessed by an oncology computer system.

As part of a radiation therapy treatment planning process, physicians may use a three-dimensional image of the patient to identify a target region (e.g., the tumor) and to identify critical organs near the tumor. They can then manually delineate the tumor that is to receive a prescribed radiation dose, and similarly delineate the critical organs that are at risk of damage from the radiation treatment. Alternatively or additionally, a computerized tool (e.g., ABAS) may be used to delineate the tumor by contouring the tumor, from which the physician may prescribe a radiation dosage. Finally, a radiation therapy treatment plan ("treatment plan" or "patient care plan") can be created such as using an optimization technique based on the clinical and dosimetric objectives and constraints (e.g., the maximum, minimum, and mean dosages to the tumor and critical organs).

IMRT planning can be a time consuming process in which a planner tries to comply with various treatment objectives or constraints (e.g., a dose volume histogram (DVH) objectives), taking into account their individual importance (called weighting) in order to produce a treatment plan which is clinically acceptable. This task can be a time consuming trial-and-error process that is complicated by the various organs at risk (OAR). As the number of OAR increases (e.g., up to thirteen for a head-and-neck treatment), so does the complexity of the process. OARs distant from a tumor are easily spared from radiation, while OARs close to or overlapping a target tumor are difficult to spare. Typically, the quality of a radiation treatment plan may depend upon the level of experience of the planner. Reducing the time to create a treatment plan is not necessarily straightforward. Further complications are caused by anatomical variations between patients.

In general practice, the initial treatment plan is not "adapted" nor improved to take into account the medical data, medical images, prior treatment (e.g., radiation therapy, chemotheapy, surgery, immunotherapy, stem cell replacement, photodynamic therapy, and the like) that is collected as the patient proceeds through a course of cancer treatment Some off-line feedback between treatment fractions (e.g., taking a new image of the tumor to determine if it has changed shape, moved or gotten smaller) may be provided. There is a need for a substantially real-time adaptive treatment management system that can interface and integrate with current hospital systems. There is a need for a real-time adaptive treatment management system that can allow the treatment planning system to acquire the relevant patient-specific data and perform predictive analysis on this data in order to provide real-time clinically meaningful information to a physician.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIGS. 6-16 illustrate exemplary interactive tasks as graphical workflows in the OIS.

DETAILED DESCRIPTION

Figure 1:
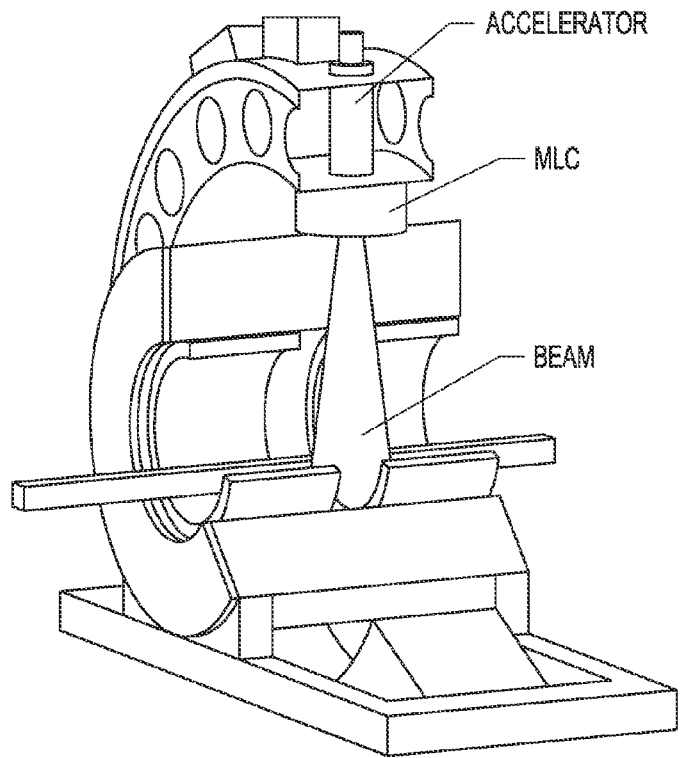
FIG. 1 depicts an MRI-LINAC, such as can be used in accordance with an embodiment of the present invention.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Physician Intent Module

One particular treatment option for a cancer patient is radiation therapy. When radiation therapy is considered as a treatment option, the physician will review relevant clinical information (e.g., past medical history, past radiotherapy treatments, chemotherapy history, performance status, medication, family history, social history and the like) and diagnostic information (e.g., results of scans, endoscopies, surgical notes, pathological notes, laboratory results and the like) as well as any other patient-specific information, in order to assess the appropriateness of recommending a course of radiation therapy to the patient at their time of consultation. Should the patient agree to undergo a course of radiation therapy, the physician may typically then do the following in chronological order:
(1) may order and schedule the patient for additional imaging (e.g. CT, 4D CT, PET-CT, MRI, MRI-PET) or functional imaging studies (e.g. PET, SPECT, perfusion CT, functional MRI (fMRI))
(2) may opt for a motion management strategy in order to determine type of simulation (e.g. gating, tracking, Active Breathing Coordinator, Abdominal Compression)
(3) order a treatment simulation session (typically CT, 4D CT, MRI, or PET-CT)
(4) may order fusions of the imaging studies to the planning dataset for the purpose of volume delineation
(5) order treatment planning to be performed such that physician-defined objectives are met.

Afterward, the physician will generally perform the following: (1) review and approve an appropriate radiation treatment plan; (2) define the type and frequency of on-going imaging to occur throughout the course of therapy for the purposes of localization; (3) use deformable registration to accumulate doses from each of the individual radiation treatment fractions onto a reference dataset to assess the progression of radiation treatment (i.e., compare the planned dose distribution to the actual dose distribution received to date); (4) choose to have the plan modified at the time of treatment, based on patient-specific changes (e.g., not merely changes in anatomy caused by e.g., weight loss, but can be general deterioration in the patient's health. The above identified tasks are typically manually performed In an example, the present adaptive treatment planning system is not limited to radiation therapy using a linear accelerator per se, but may be used for example for Brachytherapy.

These complex activities, such as described above, can be taken together to represent the physician's treatment intent for this patient. The physician intent can include not just the patient's treatment plan, but how the patient is to be treated, imaged, managed, and periodically assessed as the patient proceeds through the entire course of radiation treatment.

What is needed by an adaptive treatment management system is a user-configurable physician's intent module that allows a physician to quickly define the physician's treatment intent. Further, the physician intent module can take into account one or more parameters for imaging, simulation, treatment planning (e.g., including prescription dose, dosimetric constraints, dose volume histogram limits, whether to combine IMRT with IGRT or IMRT with simultaneous boost, and the like), image guidance, motion management, adaptive planning, and continued assessment as a patient proceeds through the course of radiation therapy. The adaptive treatment management system can be used to advise the physician. These activities cannot necessarily be separated from one another as these are sometimes dependent on each other, and can be taken together to make up the physician's intent.

The physician intent module need not be a simple "free text' repository to document what the physician desires. Instead, as part of an adaptive treatment management system, the physician intent module may define and drive the workflow and/or enforce the workflow where appropriate. The physician intent module may notify the physician of both deviations from the "patient treatment workflow", and from the expected treatment progression. The patient treatment workflow can monitor one or more radiation treatment courses, as well as provide the physician with an evaluation of the progress of the radiation treatments in the different patients. The evaluation can provide action points for the physician, such as in order for him/her to provide input to adapt a treatment plan (e.g., conventionally, there is one treatment plan per patient, and the plan is not adapted during the course of treatment). Furthermore, a clinical workflow capable of interfacing with other modules, such as the OFFLINE REVIEW and PREDICTIVE INTENT modules, such as described below, is needed.

Thus, the physician intent module can take into account a) imaging and simulation for planning definition and scheduling, b) planning target volumes and OARs definition, c) initial treatment plan, d) localization method(s) and frequency, e) adaptive planning (on-line, off-line, and real-time) definition and frequency scheduling, e) motion management definition and frequency scheduling, and f) any automatic triggers involving the above that would motivate the physician to alter the initial "plan" because there has been a deviation from his or her intent. With regard to imaging, imaging can be utilized for different purposes, for example, diagnostic imaging, simulation imaging, verification imaging during treatment, and imaging after treatment. Although each of the components of a module may have one or more dependencies, each module can be customized. The physician intent module may also include an independent template. Furthermore, the physician intent module may be capable of being edited independently.

(A) Imaging and Simulation for Planning Definition and Scheduling

The Imaging and Simulation for Planning Definition and Scheduling component of the Physician Intent Module can allow the physician the ability to order planning-specific studies, including other imaging studies, as indicated for a particular patient. This component can also allow the physician to specify the details of the simulation: e.g., treatment position specification, treatment site specification (e.g., including laterality if applicable), International Classification of Diseases code (ICD), preview request (e.g., yes/no), scan type, anatomical extent, resolution, and contrast, isocenter definition, immobilization methods and devices, bolus type and placement in-patient or out-patient delivery, 4D imaging, placement of fiducials or markers during simulation, additional imaging and fusion request, the type of treatment unit and the treatment technique, and motion management strategies. Using the present system, the physician can also schedule any imaging that needs to occur during the course of treatment, but not during the treatment session itself (e.g., schedule a PET scan after 10 fractions of the radiation therapy have been delivered, such as during separate therapy sessions). This component can be driven by a user configurable template schema that can populate either by manual selection or automatically (based on patient characterization, for example, prostate stage 1c, patient age greater than 65), and yet remain editable and utilize physician review and approval.

Therefore, in an example, the Imaging and Simulation for Planning Definition and Scheduling component of the Physician Intent Module can provide an adaptive treatment management system with at least one of the following: (a) a "menu" for the physician to choose from when specifying the details of the simulation (b) the ability to request imaging during the course of treatment if necessary, and (c) a user configurable schema.

(B) Treatment Planning Order

This Treatment Planning Order component of the Physician Intent Module can allow the physician to order a patient's treatment plan, which can include all relevant information, and clearly and effectively communicate the 'physician's intent' to the treatment planner. The planning activity can be closely linked to the simulation activity, and the planner can have access to both the treatment planning information (as ordered by the physician) and the simulation information.

There are a plurality of factors that may be included in the treatment planning order component. At least one or more of these factors can be taken into account by the treatment planning order component such as to provide the physician with a potential treatment option for a particular patient.

For example, the component may contain at least one or more of the following:
  a treatment site specification
  treatment position information
  a list of organs and volumes to be delineated
  potential instructions for auto-contour generation
  margin information, active margin indicators (e.g., margins that are automatically created in response to edits to the parent organ(s)
  isocenter placement instructions
  fusion requests, deformable registration requests
  information about how and when the fusions or deformable registration are to be approved (e.g., including when, and by whom)

treatment technique information:
(e.g., beam energy, dose rate (flattened or unflattened) linear accelerator to be treated on
dose fractionation (hypofractionation or hyperfractionation),
3D conformal
use of intensity modulated radiation therapy (IMRT, step and shoot or dynamic), volumetric-modulated arc therapy (VMAT), stereotactic body radiation therapy (SBRT), Image-Guided Radiation Therapy (IGRT), and the like.

The treatment planning order component may also include additional information such as how motion management is to be incorporated into the planning process. Some considerations to take account of motion management intent can include:
(a) maximum tumor or organ at risk (OAR) motion allowable, which phases of the respiration cycle to delineate the Gross Tumor Volume (GTV) or OAR Planning Risk Volume (PRV) on, how to unify this information to arrive at a GTV;
(b) whether to create and use a Maximum Intensity Projection (MIP) or Minimum Intensity Projection (MiniIP) over all, or delineate on a specified subset of phases;
(c) whether to base the plan on an average scan over the entire respiratory cycle, or on an average over a specified subset of phases;
(d) whether 4D planning over a subset or all of the phases is to be performed;
(e) whether or not a particular plan is to incorporate synchronization of delivery and motion; and
(f) whether or not imaging planes or volumes need to be selected at the time of planning for transfer to the linear accelerator to guide localization and/or motion management;
  a. and if (f) is true, instructions for specification of these planes or volumes.

The treatment planning order component may also include one or more factors associated with a dose of radiation to be prescribed to the patient's tumor. For example, dose information may include: bolus type, placement and frequency; number of fractions and the schedule (e.g. once or twice daily, alternate days, once weekly); total nominal dose; nominal dose per fraction; maximum dose specification and/or minimum dose specifications; dose volume constraints and/or objectives (expressed in either absolute or relative terms); dose computation uncertainty; and dose computation grid resolution. The dose specifications may include the volume limits as part of the specification, for example, no more than 2 ccs of a particular anatomical structure may receive a radiation dose in excess of 107% of the prescription dose One or more additional or alternative factors that the treatment planning order component may include are:
(a) heterogeneity objectives;
(b) conformality objectives and their definition (e.g. Vrx/Vptv where Vrx means Volume receiving greater than or equal to prescription dose, and where Vptv means Volume occupied by Planning Target Volume)
(c) functional loss tolerances (organ specific, endpoint specific, and based on biological functional modeling);
(d) Normal Tissue Complication Probabilities (NTCPs)
(e) Tumor Control Probabilities (TCPs)
(f) avoidance structures (e.g., organs at risk, or subsets of these organs designated to receive minimal dose);
(g) timing of delivery constraints (e.g., patient must be scheduled to have treatment one half hour before a chemotherapy appointment, twice daily fractions must be six hours apart, or the like);
(h) specification of geometric constraints (e.g. target or OAR volume must be less than Xccs to qualify for this technique);
(i) maximum number of control points (CPs) or segments;
(j) minimum field size per segment; and
(k) maximum Monitor Units (MU) per field, or minimum MU per segment.

Moreover, the treatment planning order component, to be more comprehensive, can take into account one or more of the following: specification of any relevant protocol rules that must be adhered to or referenced; specification of planning optimization objectives and constraints; specification of algorithm(s) to be used; specification of isodose volume limits; specification of Equivalent Uniform Doses (EUDs); and specification of Biologically Equivalent Doses (BEDs).

Thus, in an example, the treatment planning order component can be driven by a user configurable template schema that can populate either by manual selection or automatically (e.g., based on patient characterization e.g., prostate stage 1c, ICD, patient age greater than 65), and yet can be editable and can utilize physician review and approval. Thus, the treatment planning order component can provide one or more of the following types of inputs to the Physician Intent Module, as part of the adaptive treatment management system: (a) a planning activity which has taken into account simulation information, (b) a motion management recommendation, (c) a treatment planning order, and (d) a verification that protocol is being followed.

(C) Localization Definition and Frequency

The localization definition and frequency component of the Physician Intent Module can allow the physician to define the type of localization to be used at the time of treatment. For example, the localization component may define one or more actions to be taken as a result of the localization measurements (e.g., the physician desires five days of localization imaging with no action, followed by an analysis of those measurements and a couch shift of X, Y, Z millimeters before the $6^{th}$ fraction; or additionally or alternatively, for example, the physician desires an adjustment of the couch position every day if the recommended shifts exceed a predetermined amount). Additionally, it can allow the physician, if it is appropriate, to specify a volume or a position of one or more 2D planes, or one or more 1D navigator channels, to fully characterize the localization. As part of the localization definition and frequency component, another factor that may be taken into account is the frequency of the localization.

The definition of localization may include, but not be limited to, the type of imaging utilized (e.g., Megavoltage (MV), kiloVoltage (kV), Cone-Beam CT (CBCT), fluoroscopic, 3D MRI, 2D streaming MRI, 4D volumetric MRI, ultrasound, and the like) and an image matching method (bony anatomy, target, soft tissue interface, implanted fiducially matching, and the like). Additionally or alternatively, the definition of localization may include, but is not limited to, a non-image based method (e.g., optical surface matching, internal beacon positional matching, and the like). Other factors may include the particulars of each method (e.g., if the physician schedules a kV-Digitally Reconstructed Radiograph (DRR) match from orthogonal angles; if the physician specifies those orthogonal angles; if the physician requests CBCT, whether the physician specified a bow-tie filter be used, and what energy and milliamp seconds of tube current (mAS) is selected).

The physician may also identify the success criteria and decision support associated with imaging prior to treatment. For example, if the patient's movements revealed by the localization image registration with the intended treatment plan are less than a predetermined amount, the localization module can recommend to: (a) make a couch shift or (b) not make a couch shift. If the patient's movements revealed by the localization image registration with the intended treatment plan are greater than a predetermined amount, the localization module can recommend at least one of the following: (a) make a recommended couch shift, (b) perform a dose calculation, and (c) call the physician, or (d) provide an alert (e.g., other such decision support messages). The localization definition and frequency component can also inform the treatment management system to inhibit the treatment from the beginning if certain criteria set by the physician are not met.

Thus, in an example, the localization definition and frequency component can provide at least one or more of the following types of inputs to the Physician Intent Module, as part of the adaptive treatment management system: (a) a menu to assist the physician in defining the type of localization to occur at the time of treatment, (b) an analysis of one or more 2D planes (to specify a volume) or one or more 1D navigator channels, to help fully characterize the localization, and (c) a calendar to help the physician schedule the frequency of said localization.

(D) Adaptive Planning Definition and Scheduling

Adaptive planning can include at least the following three categories: a) off-line, b) on-line just prior to treatment delivery, and c) real-time (e.g., modifications made in real-time as the treatment is being delivered) and these are discussed in additional detail below. As part of the Physician Intent Module, this Adaptive Planning component can allow the physician to define, schedule, and set success criteria and actionable responses with each of the following as indicated.

A. Off-Line

The Adaptive Planning component of the Physician Intent Module may allow the physician to specify whether or not dose accumulation is to be determined off-line (e.g., while the patient is not being treated, such as in between treatment fractions or sessions), the frequency of the review of these results, and by whom. The physician can also specify any potential conditions that would automatically trigger a review notification, such as a plan re-evaluation to determine if re-planning the radiation treatment is indicated (see OFFLINE MODULE described below). Also, the physician may specify that a particular schedule for off-line planning be automatically requested and set to occur on a predetermined schedule defined by him/her (e.g., including the scheduling of any necessary re-simulation activities and additional imaging studies or laboratory tests as requested by the physician).

b. On-Line

The Adaptive Planning component of the Physician Intent Module may allow the physician to specify whether or not on-line re-planning is to be determined prior to treatment. If on-line re-planning were to occur, the physician can indicate what type of re-planning would be allowed and under what circumstances (e.g., re-plan if volumes change by a certain threshold; re-plan if plan computed metrics at the time of treatment demonstrate significant deviations from planning intent; re-plan if real or virtual shifts are larger than a predetermined amount, and the like). The Adaptive Planning component may also indicate the type and specifics of the data that would need to be collected at the radiation treatment machine, as a prerequisite to the re-planning (e.g., volumetric 3D or 4D data, and extents). Furthermore, for any on-line re-planning, the Adaptive Planning component can also indicate the type of approval (e.g., physician, planner, or physicist) that can be required.

c. Real Time

The Real Time component of the Physician Intent Module can allow the physician to specify whether or not real time re-planning is to occur during treatment. Conventional technology does not allow for real-time re-planning, though it would be advantageous to the patient to provide that capability to a physician. Real-time re-planning may include the type of re-planning that would be allowed, and under what circumstances.

The Adaptive Planning Definition and Scheduling component can provide one or more of the following types of inputs to the Physician Intent Module, as part of the adaptive treatment management system: (a) one or more potential conditions that would automatically trigger a physician review notification, (b) the physician with the ability to re-schedule any necessary re-simulation activities, additional imaging studies, or laboratory tests based on the course of treatment, and (c) the capability for a physician to perform real-time re-planning (E) Motion Management Definition and Scheduling The Motion Management Definition and Scheduling component of the Physician Intent Module can allow the physician the ability to define the type and nature of the motion management strategy to be used during the patient's treatment course. Motion management can be important because an aim of radiation therapy is to deliver a tumorcidal dose of radiation to the tumor whilst sparing healthy surrounding tissue. There are many sources of uncertainty that can occur during the course of a patient's treatment. The sources of uncertainty may include (a) random errors, (b) small changes in a patient's setup (e.g., patient is laying 1 cm to the left; it is called inter-fraction motion), (c) physiological changes (e.g., tumor size and shape changes—it can regress; patient weight loss; variable filling of the rectum and bladder), and (d) motion. Some motion may be random and unpredictable (e.g., coughing) Other motion may be categorized as being more consistent (e.g., respiratory motion, peristalsis, cardiac motion). The magnitude and shape of intra-fractional motion can vary considerably among tumors and patients. For example, some patients breathe quickly and others may take shallow breaths.

The Motion Management Definition and Scheduling component may include gating (e.g., controlling timing of radiation delivery), tracking (e.g., controlling spatial direction or location of radiation delivery), or a combination thereof. These motion management methods may involve auto-segmentation, deformable registration, 2D/3D rigid registration, or deformable registration for locating the target relative to the tracking envelope. The motion management strategy may also include 2D/3D registration or 3D/3D registration to a particular phase of the respiratory cycle on a 4D imaging study. Motion management strategy may also define tracking channels, planes or volumes.

The Motion Management Definition and Scheduling component may further include, for a physician, the ability to define the delivery of a synchronized plan (e.g., a plan that has been optimized using a method to include or adjust for the effects of motion in a synchronized fashion).

In an embodiment, the motion management strategy may include gating. Therefore, the Motion Management Definition and Scheduling component can further include one or more control parameters for the type of gating and the gating window (e.g., spatial and/or temporal). Various examples of gating may be utilized, separately or in combination. One example of a spatial gating window may include the use of a 1D respiratory waveform over 30% of the waveform. Another example may include using a 2D respiratory waveform with the target envelope. In an example, a combination of a 1D respiratory waveform and a 2D respiratory waveform can be used, such as with the 1D respiratory waveform as the master and the 2D respiratory waveform as the slave, or vice versa. In an example, a spatial gating window may utilize a 3D respiratory waveform with the target envelope to determine the gating window. Furthermore, an example of a temporal constraint can be to allow deviation from the envelope for a predetermined period of time (e.g., X seconds) before gating the beam off. This can extend an approach to gating that allows leaving the beam on, instead of gating the beam off instantly when the target is measured or predicted to have moved outside the gating window. Using this method repeatedly can provide flexibility such as by the temporal constraint allowing the gating window to be violated by up to a predetermined amount of time (e.g., X seconds) before the beam is gated off.

In an embodiment, the motion management strategy may include tracking. Therefore, the Motion Management Definition and Scheduling component can further include the ability for the physician to define a tracking methodology. For example, the physician may choose to track the centroid (e.g., center of mass) of a fixed shape, which may be done either using a rigid representation or a deformed shape of the target (e.g., no change in the shape of the apertures, instead, tracking maintains the relative location of the centroid with respect to the fixed shape). In an example, the physician may select to use shape-based tracking (e.g., alter the apertures based on the changes to the shape of the target). Shape-based tracking, for example, may be utilized in the case of the delivery of a dynamic conformal arc.

As part of the tracking methodology, the physician may provide a tracking maximum (e.g., track up to X cm then gate the beam off, or until the target no longer violates this tracking constraint). The physician may specify which organs not to track the beam near to or over (e.g. track the target tumor unless the target tumor gets within X mm of the spinal cord and then gate the beam off until the target no longer violates this constraint).

Another aspect of The Motion Management Definition and Scheduling component can include accounting for system latency. For example, the physician may choose from different predictive models to account for system latency. The physician may utilize a training time for the predicative models, and may define whether or not original motion information captured at the time of treatment is used to initialize these models.

Furthermore, the Motion Management Definition and Scheduling component may provide the physician with the ability to preview one or more factors included in the Motion Management Definition and Scheduling component of the Physician Intent Module prior to treatment.

Thus, the Motion Management Definition and Scheduling component can provide one or more of the following types of inputs to the Physician Intent Module, as part of the adaptive treatment management system: (a) factors to define the type and nature of the motion management strategy, (b) a physician with the ability to select the delivery of a synchronized plan (c) a selection of types of gating windows (d) a menu of options for a tracking methodology, (e) a plurality of predictive modules to help the physician account for system latency.

(F) Automatic Triggers

In an example, part of the Physician Intent Module can include the ability to specify one or more triggers and tolerances that can notify one or more individuals of actual or predicted deviations from the physician's therapeutic intent. The notifications may be caused either by deviations in the intended workflow, or changes in the patient's condition (alteration in physical or mental status, disease progression or regression, or the like). These notifications may occur as a result of off-line analysis, or may occur in real-time (at the linear accelerator at the time of treatment) based on the most current imaging, segmentation, dose computation, optimization or predictive results. The user can be then prompted to view certain specific results and/or guided in making a decision. For example, see the OFFLINE ASSESSMENT Module below for more information specific to the types of triggers that may exist.

Predictive Analytics Module

Cancer affects more than 14.1 million patients a year and as a chronic illness causes more than 8.2 million people to die every year. One method to treat cancer is to use radiation therapy which can be given for example, over a course of 42 treatment sessions or fractions. A reason for a fractionated radiation delivery is mainly because of human cell biology: a healthy cell can usually recover faster from radiation damage, whereas a cancer cell will be lethally damaged and unable to replicate.

For each treatment, a number of data points can be collected. A typical medical clinic that provides radiation therapy may see 20-30 patients a day per radiation therapy machine. Over the course of treatment, for each patient there is a significant amount of medical information available for a physician to review. In addition, over 80% of stored information is unstructured. Furthermore, data may include multiple types of information ranging from imaging (e.g., CT, X-ray, radiotherapy portal images, magnetic resonance imaging (MRI) images, positron emission tomography (PET), single-photon emission computed tomography (SPECT), and the like) to clinical information (lab results, weight, performance status, pain and breathlessness scores, and the like). Therefore, a method of using predictive technology as part of the adaptive treatment management system to provide the physician or healthcare worker with early warnings of impending clinical problems, which can greatly improve patient care and prevent expensive medical crises.

The amount of data/information available has an enormous potential for improving diagnostic accuracy, treatment selection and outcome. Merely having a large amount of data alone does not translate into improved diagnosis, treatment selection, outcome, or even indicate when a particular treatment regimen may need to be altered. What is needed are predictive models and data mining algorithms that extract key information, as part of the adaptive treatment management system, to provide clinically significant actionable information and hence ensure improved patient outcomes. For example, in order to improve patient outcomes, the Predictive Analytics Module may determine the right subset of patients who would benefit from a particular treatment or combination of treatments (e.g., chemotherapy, radiation therapy, concurrent chemo-radiotherapy, surgery), and thereby advantageously reduce the cost and increase the efficacy of the overall treatment for a patient. Furthermore, comparing individual patient specific features to a large database of previously treated patients' data may be used to predict individual patient response to a treatment, as well as personalize that patient's treatment to optimize their outcome. Once a course of radiation therapy has been decided, the therapeutic process can be monitored such that, via the use of predicative analytics, the medical team may predict when that course of treatment is deviating from the physician intent, or when anatomical, functional, or disease-related changes occur that warrant intervention and alteration of the original therapeutic plan in order to optimize that patient's outcome.

There is a need to provide predictive analytics for the management of patients with cancer. There is a need to collect a patient's physiological and anatomical information as a patient proceeds through a prescribed course of radiation treatment over a length of time. There is a need for a system of automated alerts to assist the physician in recognizing when there is a necessity to alter the original plan based on information gathered during the course of therapy, and in order to optimize that patient's outcome.

The Predictive Alerts Module can relate to the Off-line Review Module as well as the Physician Intent Module, as part of the adaptive treatment management system. For example, based on the physician intent for the treatment of a particular patient, a plurality of data can be saved per patient. These data may include a plurality of simulation and localization image data, functional imaging data, delineation data, dosimetric data (including specific dosimetric endpoints), and the like. The Predictive Alerts Module can analyze the data and interpret the results in a clinically meaningful manner using predictive analytics. The Predictive Alerts Module may include one or more prognostic factors (e.g., a measurement that defines the effect of patient or tumor characteristics on the patient outcome, and therefore provides information on the likely outcome of the cancer disease in the untreated patient) and predictive factors (e.g., a measurement that defines the effect of treatment on the tumor and patient, such that it helps to identify subpopulations of patients most likely to benefit from a given therapy, as well as suffer fewer resultant toxicities).

The predictive analytics can be associated with the Off-line Review Module such as in order to provide predictive alerts for a physician to adapt a radiation therapy plan. For example, predictive alerts may include at least one or more alerts concerning predicting deviations from expected values, such as high or low dose alarms, specific Region Of Interest (ROI) Dose Volume Histogram (DVH) based alarms, percentage or absolute volume deviation based alarms, changes in Tumor Control Probability (TCP) or Normal Tissue Complication Probability (NTCP) alarms, alarms around functional changes, or alarms concerning changes in Biologically Effective Doses (BED).

The Predictive Alert Module can be more than merely a text-based search, but it can also include a mechanism to provide a biologically significant match. In an embodiment, inputs to the Predictive Module can include clinical data (such as described below), dose-volume metrics, functional organ information, and molecular biology information. For example, the Predictive Module can take into account individual patient's genomic expression under different environmental conditions (such as during a course of radiotherapy), the different cell types of interest in that patient and their stage within the cell cycle.

Data input to the Predictive Module may include information such as one or more of imaging data (e.g., MRI, CT, X-ray, PET, SPECT), organ or volume of interest segmentation data, functional organ modeling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (e.g., blood pressure, temperature, respiratory rate), genomic data (e.g., genetic profiling), demographics (e.g., age, sex, ethnic origin), other diseases affecting the patient (e.g., cardiovascular or respiratory disease, diabetes, radiation hypersensitivity syndromes), medications and drug reactions, diet and lifestyle (e.g., smoking or non-smoking), environmental risk factors, tumor characteristics (e.g., histological type, grade, hormone and other receptor status, tumor size, vascularity), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα, and the like).

The Predictive Alert Module can analyze some or all of the vast amount of information available to a physician such as in order to provide meaningful information on the potential outcomes, if the current course of treatment based on a priori evidence were followed. For instance, gamma analysis may be used to determine, if a particular treatment deviation was to be continued for a pre-determined number of fractions, at what point would a threshold triggering a response be reached (e.g., 5% of an organ dose/volume relationship). This can be organ dependent. Furthermore, these metrics are not limited to gamma analysis, for other linear and non-linear methods to trend or curve-fit data may be utilized.

As an increased amount of data is provided to the Predictive Module over time, the predictions will improve. As such, the Predictive Module may utilize one or more of artificial intelligence algorithms, neural networks (e.g., including deep learning), genetic algorithms, machine learning algorithms, predictive analytics, k-nearest neighbor algorithms, support vector machines, majority classifiers, or other algorithm types to improve predictions. For example, there are a multitude of machine learning algorithms that can be utilized. These machine learning algorithms can be classified under the following categories: supervised learning (e.g., informational fuzzy networks, random forests, nearest neighbor algorithm, logistic model tree, and the like), statistical classification (e.g., decision trees, Bayesian networks, linear classifiers, and the like), unsupervised learning (e.g., artificial neural network, expectation-maximization algorithm, data clustering, and the like), association rule learning (e.g., a priori algorithm, éclat algorithm, FP-growth algorithm), hierarchical clustering (e.g., single-linkage clustering and conceptual clustering), partitional clustering (e.g., K-means algorithm, fuzzy clustering), reinforcement learning (e.g., monte carlo method, Q-learning, temporal difference learning, and the like.) and combinations thereof. In an embodiment, the algorithms may construct profiles consisting of genetic and environmental risks in order to determine a causal mechanism for the disease. Such algorithms may be used to provide predictions, but may also be used to optimize treatment results.

As an example of a neural network, deep learning is a set of algorithms in machine learning methods based on learning representations. These representations make it easier to learn a variety of tasks. For example, a computer can be provided with a large dataset and, by using deep learning algorithms, can sort the elements of the data into categories such as function, shape or other. A "clustering" may occur based on the similarity of data. Advantageously, deep learning uses models to learn categories incrementally, e.g., learning lower-level categories before attempting to learn higher level categories. An assumption is that there are unforeseen configurations in the categories that allow them to be organized into multiple levels that correspond to different levels of abstraction. What is learned at each level is fed to the next level (e.g. training). Potentially as the number of levels increases, the errors shrink exponentially. Therefore, deep learning is a form of unsupervised learning that can be used to integrate abstract knowledge, such as vast medical data.

Part of the process of data analysis may include data mining (e.g., may be termed knowledge discovery). Data mining is essential to improve methods of diagnosis, disease prevention and treatment. One purpose of data mining is to determine patterns within large datasets, and thereby extract useful information that can be used later. Note that not all data is transaction-based and logical. Therefore, inexact rules may be present within the dataset. The actual data mining process may include an automatic or a semi-automatic analysis to uncover previously unknown patterns within the dataset, and does this by using, for example, cluster analysis, anomaly detection, multifactor dimensionality reduction, and association rule mining (e.g., pattern mining, subject-based data mining) Other examples include using Bayes theorem and regression analysis to identify patterns. Data mining can also use algorithms used in the areas of neural networks, cluster analysis, genetic algorithms, decision trees, as well as support vector machines.

In an example, data mining can include the following tasks: anomaly detection (e.g., identification of unusual data records), association rule learning to determine relationships between variables, clustering of structures without using known structures, classification (e.g., generalizing a known structure and applying it to new data), regression (e.g., determining a function that may model the data with least error), and determining the results (e.g., providing a report). Therefore, data mining can be useful in analyzing vast amounts of data to determine trends and create sophisticated algorithm which may aid in the final decision analysis. For instance, sophisticated algorithms may be utilized to decide, in real-time, when to provide an alert for the physician.

The Predictive Alert Module can transform data into knowledge, to be considered by a physician in the present time, as well as help them plan for the future. The Predictive Alert Module can offer end users the choice to explore cause and effect relationships in the data. In an embodiment, the users' experience may be graphical, visualizing large datasets with an approachable and navigable interface, allowing users to pose "what-if" questions in real-time, and analyze potential outcomes, and select appropriate pathways. The data visualization can allow drilling into the graphic datasets, and re-arranging metrics to ask questions in different ways. Potential outcomes can then be saved as an individual user's personal "wisdom agent", for later reference and further exploration of the information. In an example, the Predictive Alert Module may utilize vast amounts of data using machine learning algorithms to interpret real-time changes and thereby provide various treatment adaptations in real-time.

Certain events may automatically trigger a notice to a physician in the Off-line Review Module. These predictive alerts may include, for example, target underdose, Tumor Control Probability (TCP) below a preset threshold, Normal Tissue Complication Probability (NTCP) above a preset threshold, percentage chance of local recurrence above a preset threshold, inadequate target dose coverage of local lymph nodes where probability of lymph node involvement is above a preset threshold. Furthermore, the predictive alerts may indicate to the physician that the radiation therapy treatment plan should be adjusted or adapted, based on the predictive information.

The Predictive Alert Module, as part of the adaptive treatment management system, can be advantageous for a physician for it can help to determine whether a patient will need to be re-planned on a daily basis, based on historical data. For example, the Predictive Alert Module may allow a physician to visualize the dose given to a patient, as well as any geometric discrepancies as the dose accumulates in various organs during the course treatment. Furthermore, the Predictive Module may take into account tumor regression, predict changes in OAR position relative to the target volume (e.g., is the parotid gland moving into the planned treatment field, and the like), identify genetic markers, and determine what changes occur as treatment continues. The Predictive Alert Module can enable physicians to use machine learning algorithms, for example, to analyze a large number of patient data in order to efficiently and rapidly create and modify "smart" treatment plans without the need for burdensome trial-and-error iterations.

Off-Line Review and Assessment Module

A typical medical clinic that provides radiation therapy may see at least 20-30 patients per day, and a physician may have multiple things to review daily, from patients themselves, their vital signs, their images, their doses, as well as adjustments to their treatment plans in an adaptive radiotherapy environment. Even now, there may be an overwhelming amount of information for a physician to review, and a critical piece of information may fall into a chasm and be missed because of the volume of information.

What is needed from an adaptive treatment management system is a decision support system for items that a physician must review in an adaptive radiation therapy environment. The decision support system needs to provide, in a visual manner such as a dashboard, information typical of a quality assurance checklist, as well as information that a physician would consider essential, even critical.

The Off-line Review Module and Assessment Module can include one or more of the following tasks to be performed by a physician or physicist (e.g., may be a list of patient information to review, a list of "things to do today", and the like): (1) image review, whereby the physician reviews daily images (e.g., 2D, 3D, 4D, motion view X-ray, MRI, ultrasound, and the like) taken at the machine for the specific purpose of assessing whether the patient was set up in an anatomically correct manner; (2) review of the image registration performed at the machine, which may lead to re-registration of the images, approval, comment, and/or further instructions for the therapist.

The Assessment Module can provide the ability to review both images and dose, such as in order to assess whether the patient is set up correctly and receiving the intended fractional or cumulative dose.

Registration Review (e.g., performed by a healthcare worker, for example a physician)

The user can examine the result of a rigid and/or deformable registration between a planning image and the most recent fractional image. Tools can be provided by the Registration Review to indicate to the user those areas of higher uncertainty regarding the deformation results (e.g., display regions of "large" deformations, or apply the deformation to the original image and do a "delta" to show areas with differences). If the result is unsatisfactory, the user may either abandon the adaptive planning procedure, or use available tools to improve the deformable registration result.

Segmentation review (e.g., may be performed by a physicist and/or a physician)

The user can examine the deformed versions of the critical and target structures taken from the planning image superimposed on the most recent fractional image. If the result is unsatisfactory, the adaptive planning procedure may be abandoned, or the user may use available tools to edit the segmentation results and feed those back to improve the quality of the deformation field. In an example, a medical re-evaluation may need to be performed on the patient resulting in a new treatment plan being developed. For example, the assessment may determine that a significant proportion of abandoned plans result from patient weight loss that requires medical intervention.

Fractional Dose Review (e.g., may be performed by a physicist and/or physician)

The user can examine the most recent fractional dose or fractional biologically effective dose (BED), Tumor Control Probabilities (TCP) or Normal Tissue Complication Probabilities (NTCP) calculated using the deformable registration between the planning image and most recent fractional image.

Treatment Delivery Review (e.g., may be performed by a physician)

The user can examine the dose or BED or TCP or NTCP reflecting the treatment to date (e.g., the sum of all the current fractional doses or dose equivalents).

Treatment Dose Statistics (e.g., may be performed by a physician)

The physician can examine DVHs, dose statistics, dose isocontours, TCPs and NTCPs reflecting the treatment to date, as well as fraction-by-fraction trends related to doses, BED, NTCPs, or TCPs received by critical and target structures.

ROI Statistics (e.g., may be performed by a Physician)

The user can examine the trending of Regions of Interest (ROIs) (e.g., volumes shrinking/growing or centroids translating) to detect one or more trends that may cause the user to anticipate the need for plan adaptation. Based on the trends and statistics, a medical re-evaluation of the patient may be required.

The Off-line Review Module and Assessment Module can interface with the Physician Intent Module. For example, based on the physician intent for the treatment of a particular patient, certain events may automatically trigger a notice in the Off-line Review Module. The event may cause, for example, a physician to be notified to review one or more images, doses, and whether the radiation treatment plan needs to be adjusted or the patient needs to be evaluated for a potential medical intervention.

In an example, the Off-line Review Module and Assessment Module can allow a physician to review a plurality of patient-related information. The Off-line Review Module can provide the physician with the ability to review a plurality of data (e.g., images, dosages, biologically equivalent doses (BED), molecular information, tumor activity, and the like) for one patient at a time, or for multiple patients in an organized efficient manner. For example, the Off-line Review Module may also provide the physician with the ability to compare images from different patients, particular doses to targets and OAR from different patients, accumulated doses of different patients, and the like.

By using the Off-line Review Module and Assessment Module, a physician can determine if the radiation therapy is within tolerance of the initially prescribed plan. Based on the accumulated dose to the target tumor, the accumulated dose to organs at risk, and other factors such as tumor response, the physician may want to adapt the radiation treatment plan (e.g., on a daily basis, a weekly basis, and the like).

In an embodiment, the dashboard may provide real-time updates (e.g., real-time events that the physician needs to respond to, such as an update on an accumulated dose, a new patient image, and the like). In an embodiment, the patient may be in the process of receiving a fraction of radiation therapy, and an event may be generated requiring a physician's immediate attention.

The dashboard may provide a visualization of a physician's work-flow providing tasks for the physician to perform/review based on the physician's intent. For example, the dashboard may provide icons or other visualization methods to inform a physician of the need to contour on a patient image, review a contour, review an image, review a dose, review an accumulated dose, and the like. In an example, the events to be reviewed by the physician may include predictive results indicating trending and treatment anomalies. An example of trending would be a graph showing the percentage coverage of the parotid gland by the prescription dose, for each consecutive treatment fraction. Three examples of treatment anomalies include:

1. In a treatment fraction, the parotid gland percentage coverage by the prescription dose is twice as high as in the original treatment plan;
2. In a treatment fraction, the Planning Target Volume (PTV) coverage by the prescription dose is 10% lower than in the original treatment plan; and
3. In a treatment fraction, the overall maximum dose exceeds that of the original treatment plan by more than 10%.

Therefore, the dashboard can assist the physician by facilitating and improving the assessment of a patient's radiation therapy regimen.

In an embodiment, the dashboard may include a heat map coding (e.g., red, yellow, green colors and the like) that can indicate to the physician the priority of certain tasks (e.g., a physician can indicate beforehand what would trigger a high versus a low priority). The heat map coding may also indicate, for example, the status of a task (e.g., if a task has been completed, or what additional information is needed, or if a task is not completed).

Furthermore, the dashboard may include, for example, one or more triggers that can alert a physician to review certain items based on particular results. Some of these results may include quality measures and goodness measures which can be calculated in real-time.

In an embodiment, the Off-line Review and Assessment Module may also include one or more assessment tools. These assessment tools can include, for example: DVHs and dose statistics reviews for individual fractions as well as for the treatment to date; TCP and NTCP computations; daily images with superimposed dose isocontours allowing dose reviews on either daily or planning images; trending tools showing the changes in various parameters (e.g. volume coverage for various structures, maximum/minimum doses with respect to different structures per treatment fraction). These assessment tools can be used to analyze patient progress.

In an embodiment, the Off-line Review and Assessment Module dashboards may be provided to assist a physician in the analysis of a patient's progress. These assessment dashboards may be designed to include at least one or more of the following methodologies:

Intent Driven Schedule
In an illustrative example of an intent driven schedule, the physician can decide at the beginning of treatment that an intra-fraction image will be taken every two fractions, followed by a cursory review. Every six fractions, there will be a review of planned dose versus delivered dose to date. Every ten fractions, there will be a full review of delivered dose versus planned delivered dose in terms of trends and isocontours.

Event Driven Actions
For example, an event driven action can be one in which some external parameter (e.g. patient weight, physician observation of patient's condition) would trigger a review of the planned dose versus the delivered dose.

Predictive or Anomaly Driven Actions
A predictive or anomaly driven action, for example, can be a review that may be triggered by a change in an actual or extrapolated parameter (e.g. dose to a critical structure, dose coverage of target by prescription dose, magnitude of deformation in the deformable registration of planning and fractional images) outside a preset threshold.

In an embodiment, the Off-line Review and Assessment Module may be customized, for example, for a particular operator (e.g., a physician, a physicist, and a health care worker).

FIG. 1 depicts an example of an MRI-LINAC combination, such as can be included in or coupled to an Oncology Information System (OIS) according to an embodiment of the present invention. A cut-away view of the MRI is shown with around it the gantry with the accelerator and its peripherals. An accelerator, a multi-leaf collimator (MLC), and a beam are illustrated. A low magnetic field zone outside the MRI can be created by adapting the active shielding in order to decouple the MRI and the accelerator.

Figure 2:
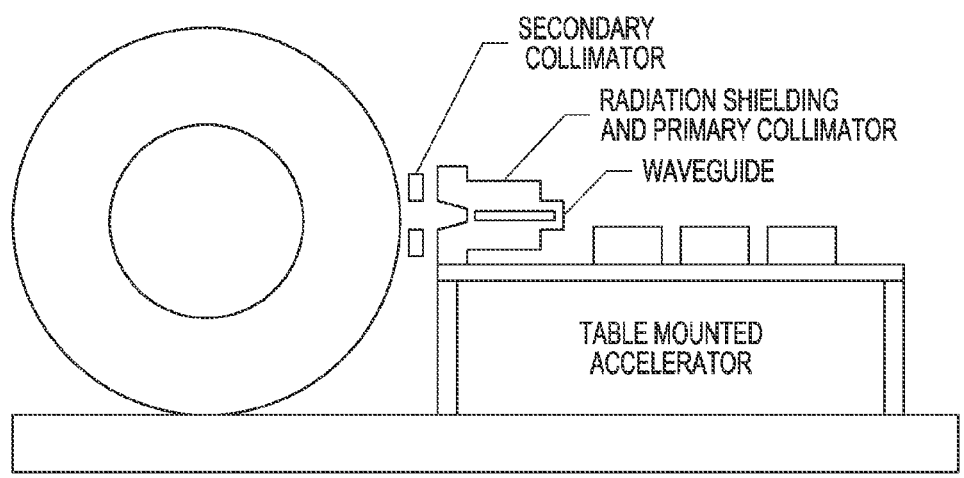
FIG. 2 is a schematic view of the MRI-LINAC shown in FIG. 1, such as can be used in accordance with an embodiment of the present invention.

FIG. 2 is a schematic view of the MRI-LINAC shown in FIG. 1, such as can be included in or coupled to an OIS in accordance with an embodiment of the present invention. In the example of FIG. 2, the acceleratory can be in a fixed position, such as lateral to the MRI. An MRI magnet, a radiation shielding and primary collimator, a secondary collimator, a waveguide, and a table mounted accelerator are shown.

Figure 2A:
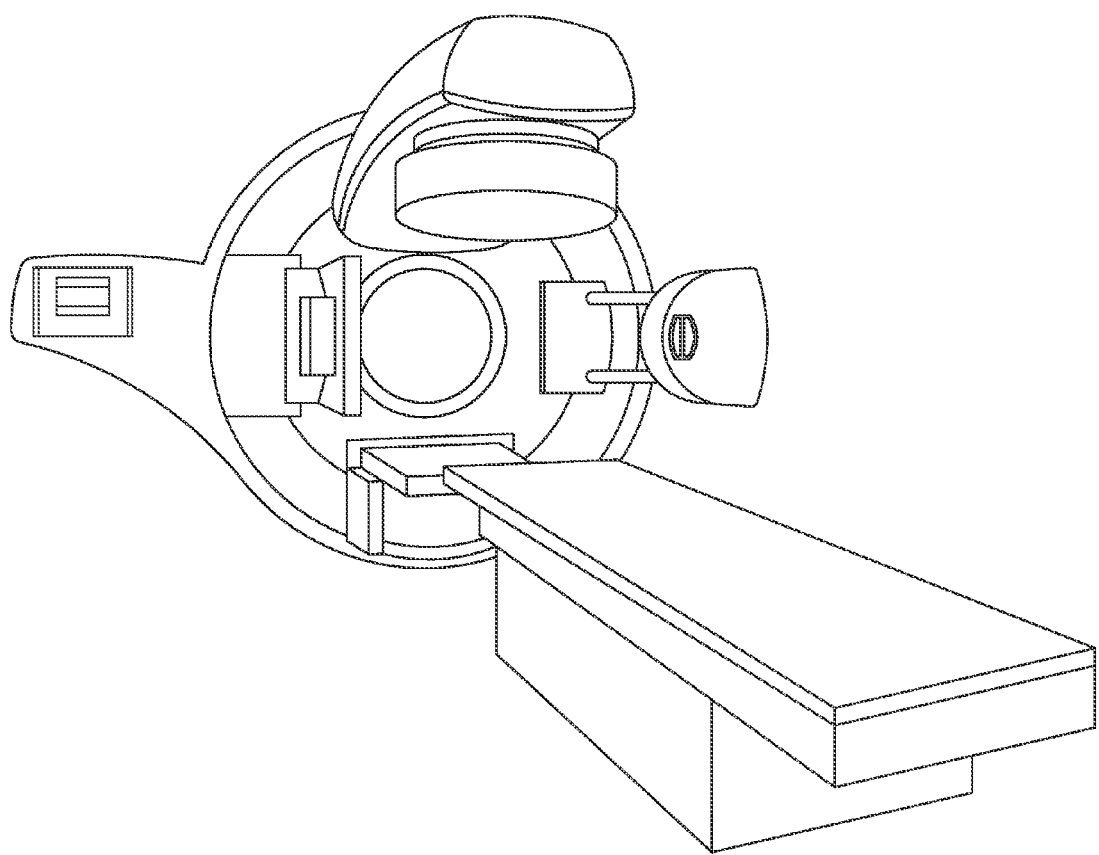
FIGS. 2A and 2B are examples of views of a linear accelerator such as can be used in accordance with an embodiment of the present invention.

FIG. 2A is a photograph of the Elekta Versa HD™ linear accelerator system such as can be used in accordance with an embodiment of the present invention, such as by being included in or coupled to an OIS in accordance with an embodiment of the present invention.

Figure 2B:
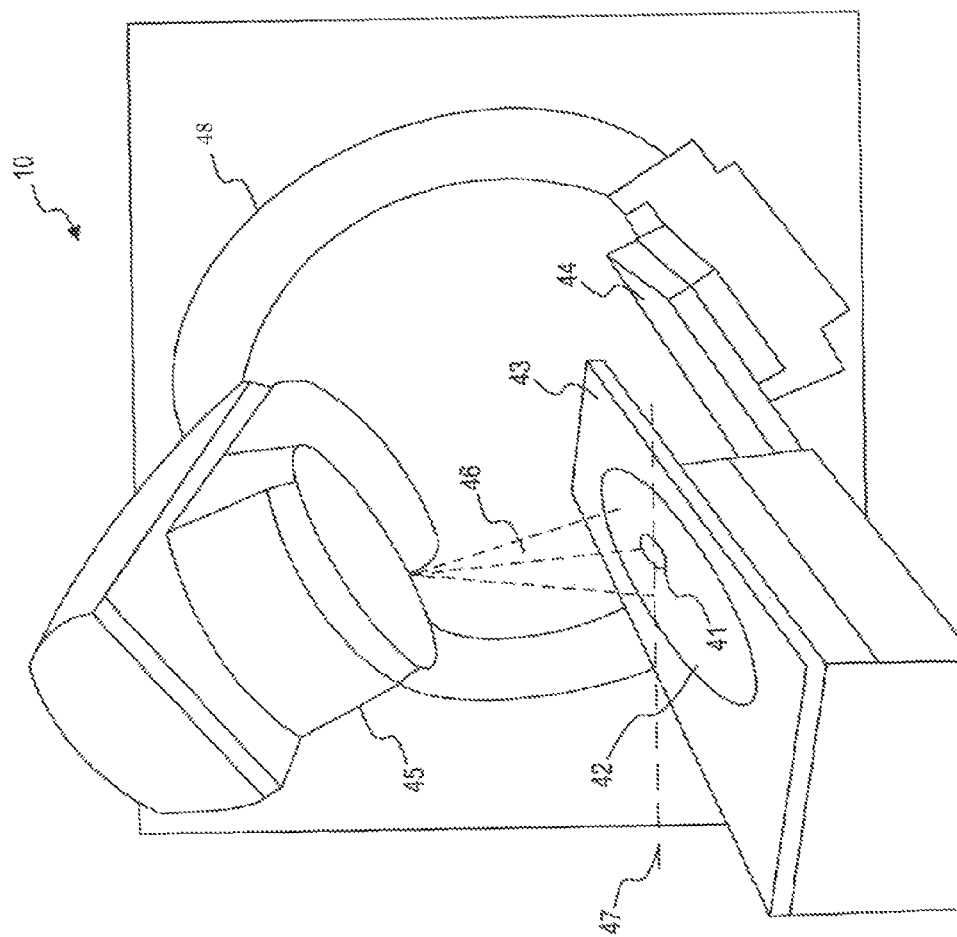

FIG. 2B illustrates an example of a radiotherapy device (e.g., a linear accelerator 10), according to some embodiments of the present disclosure. Using a linear accelerator 10, a patient 42 may be positioned on a patient table 43 to receive the radiation dose determined by the treatment plan. The linear accelerator 10 may include a radiation head 45 that generates a radiation beam 46. The entire radiation head 45 may be rotatable, such as around a horizontal axis 47. In an example, below the patient table 43 there may be provided a flat panel scintillator detector 44, which may rotate synchronously with radiation head 45, such as around an isocenter 41. The intersection of the axis 47 with the center of the beam 46, produced by the radiation head 45, can be referred to as the "isocenter". The patient table 43 may be motorized so that the patient 42 can be positioned with the tumor site at or close to the isocenter 41. The radiation head 45 may rotate about a gantry 48, such as to provide patient 42 with a plurality of varying dosages of radiation, such as according to the treatment plan.

Figure 2C:
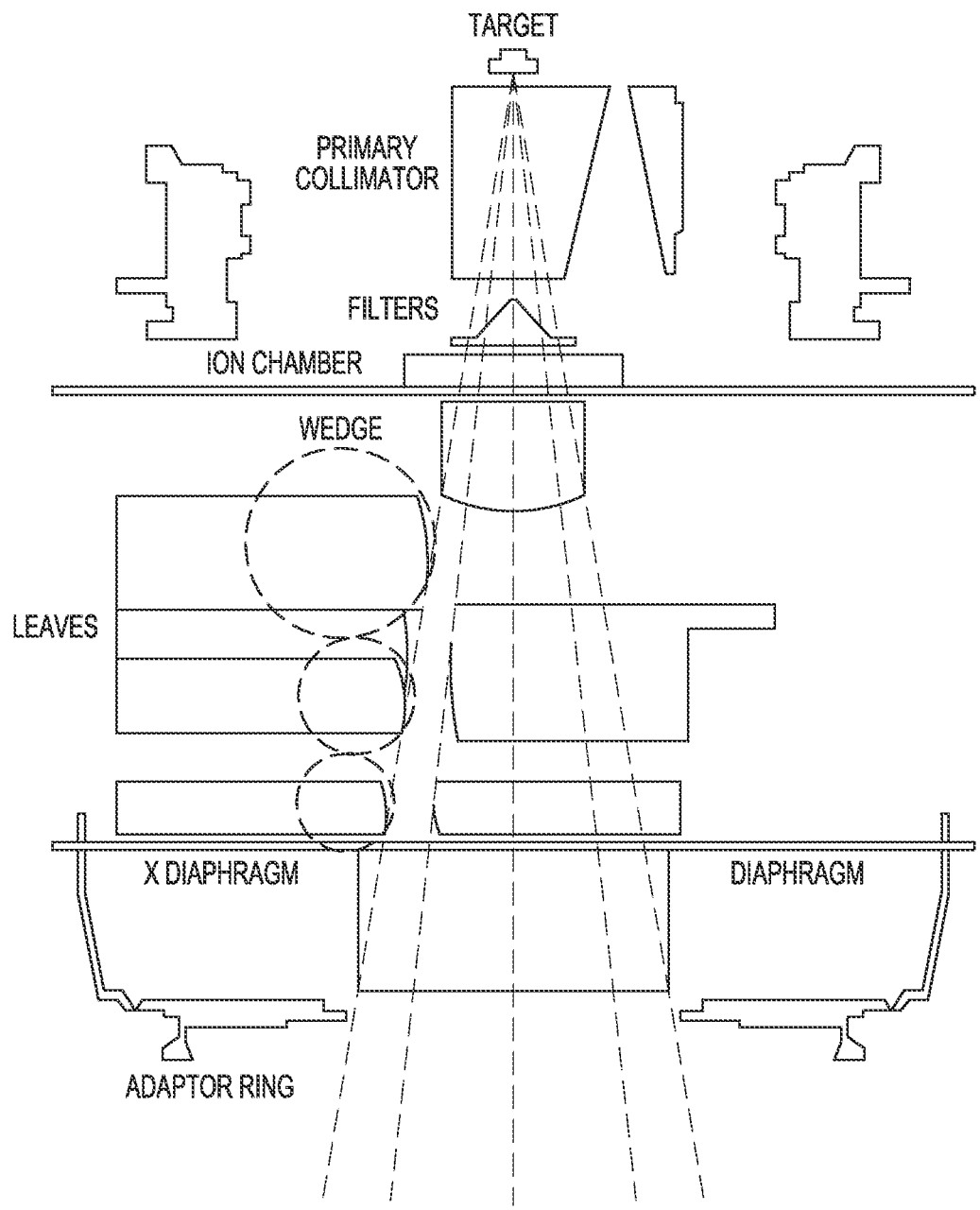
FIG. 2C is a diagram depicting an example of a multi-leaf collimator.

FIG. 2C is a diagram depicting an example of a multi-leaf collimator (MLC), which can include or interface with, leaves, a diaphragm, an adapter ring, an ion chamber, one or more filters, and a primary collimator.

Figure 2D:
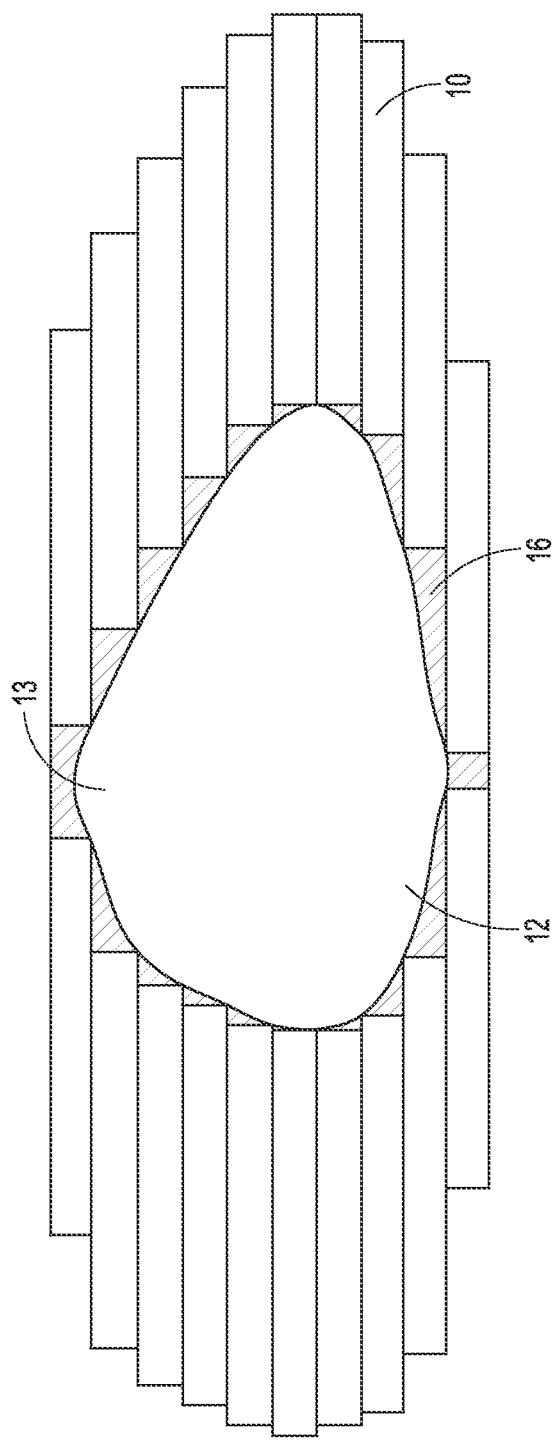
FIG. 2D is an example of an illustration of how the leaves of a multi-leaf collimator may block radiation and allow a specific area only to be irradiated.

FIG. 2D is an example of an illustration showing how the leaves of a multi-leaf collimator (MLC) may block radiation such as to allow a specific area only to be irradiated, such as according to an initial or adapted patient care/treatment plan in accordance with the present disclosure. Leaves 11 of the MLC can move laterally in a plane that is orthogonal to a beam of radiation being delivered by a radiation source to a tumor or other target 12 area to be irradiated. Adjacent leaves 11 can be controllably moved toward or away from each other, such as to create an aperture 13 allowing delivery of radiation through the aperture 13 to the target 12, but possibly also allowing delivery of the radiation through the aperture 13 to a non-target area 16 to which radiation is not intended to be delivered, but to which radiation may be delivered such as due to the "steps" in the aperture profile that are created by the finite widths of the leaves 11 of the MLC.

Figure 3:
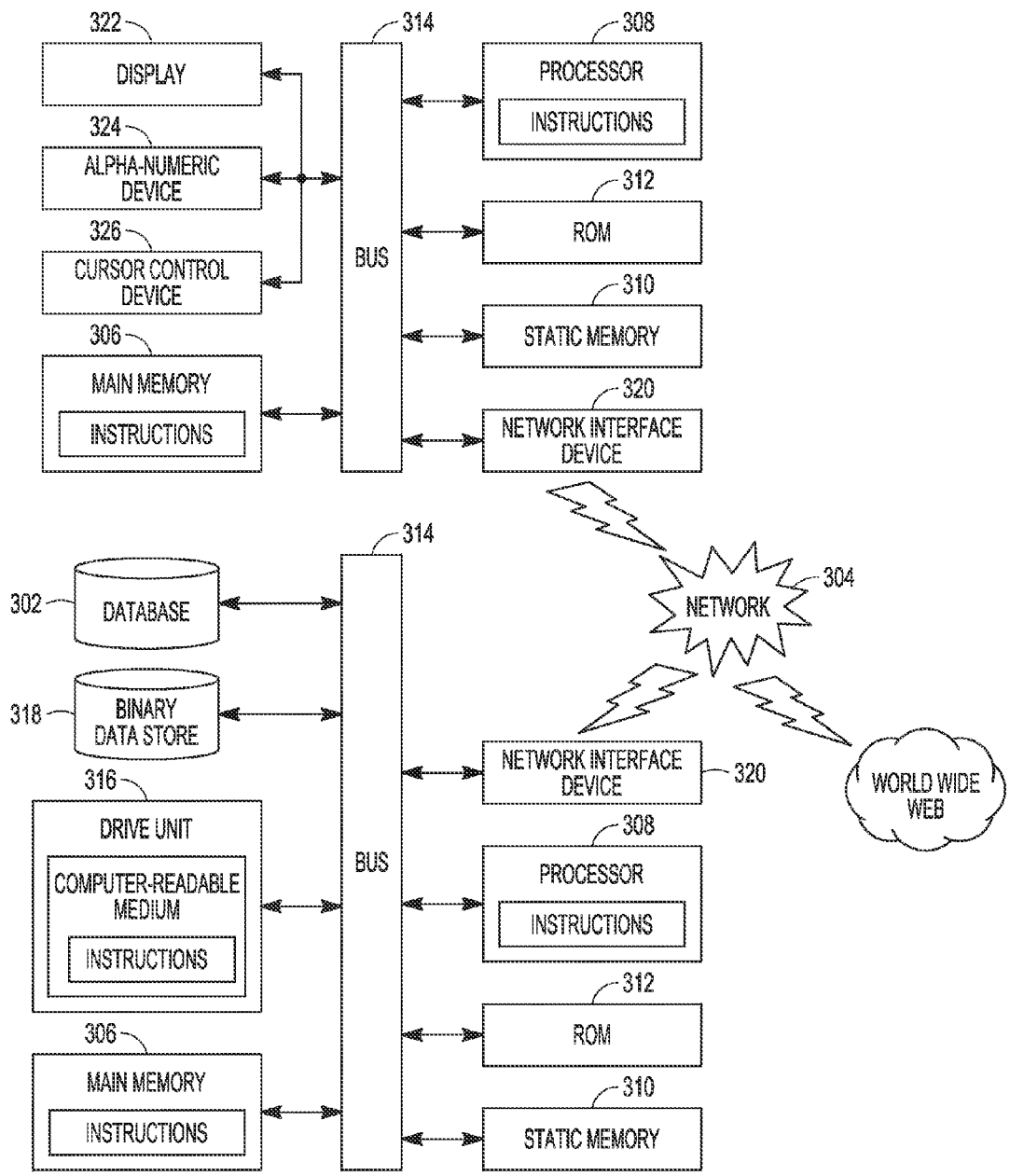
FIG. 3 is an example of a system block diagram depicting an embodiment of portions of the invention as part of an Oncology Information System (OIS).
Figure 3A:
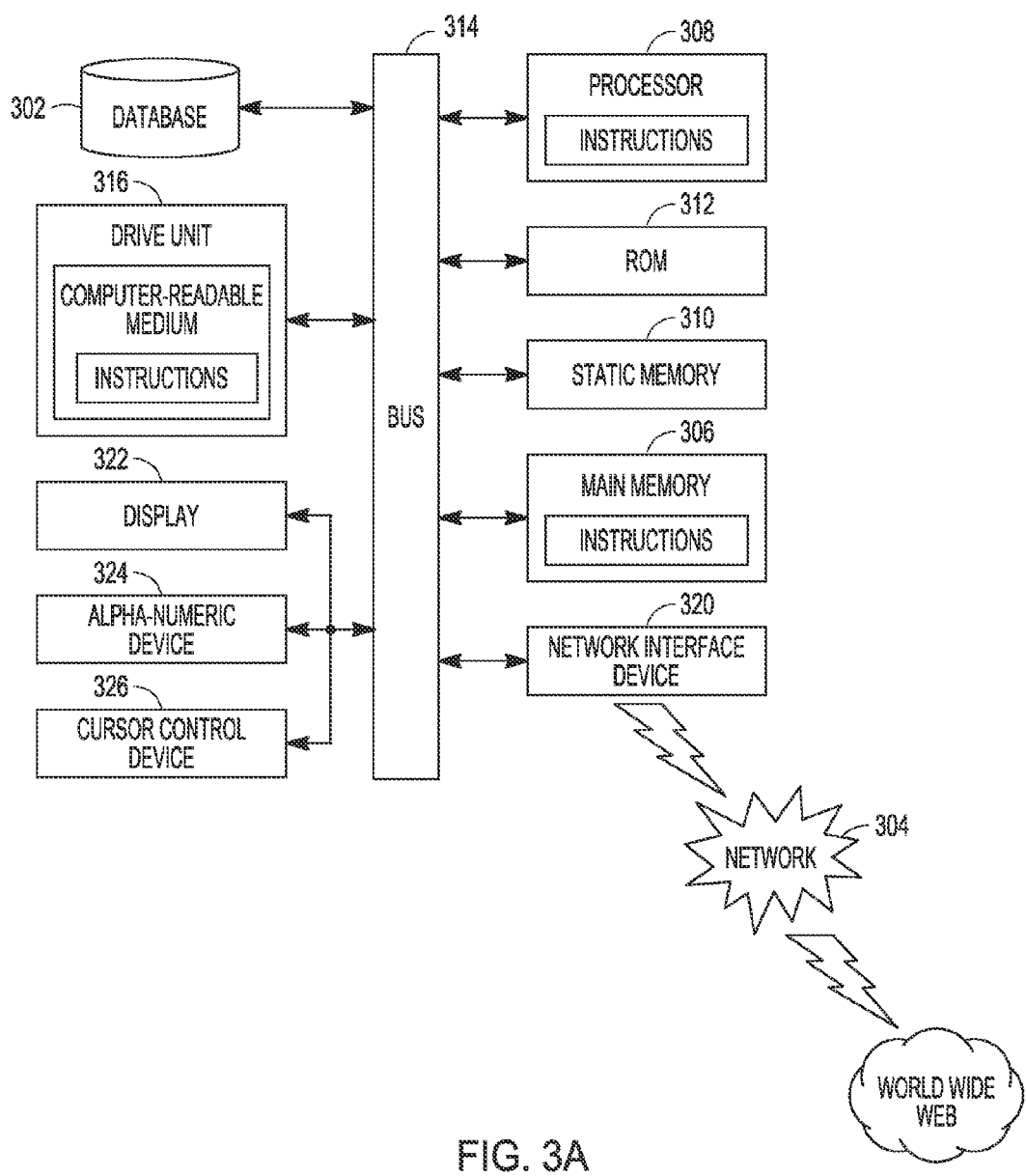
FIG. 3A is an example of a system block diagram depicting an embodiment for an OIS.

FIG. 3 is an example of a system block diagram depicting an embodiment of the invention as part of an Oncology Information System (OIS). FIG. 3A is another embodiment. The OIS environment is not intended to suggest any limitation as to the scope of use or functionality of any aspect of an OIS system as it pertains to this invention. An OIS can include or interface with a server containing the common database 302 and other related files representing the data for patients under treatment. An OIS can include one or more clients that are connected to the server via a network 304. The server can also include the stored program files that are used to load the software on to the client. The server can include a main memory into which computer instructions can be loaded, a processor 308 to execute or otherwise perform the instructions, and a static memory 310 that stores data related to the currently executing program. A read-only memory (ROM) 312 can contain computer instructions related to starting the server and to the operation of hardware devices attached to the server. A system bus 314 conveys data between the components that make up the server. A drive unit 316 attached to the server can contain computer instructions for various software programs that make up the OIS. These instructions can be loaded when the user desires them to execute functionality of the OIS, or when system events occur that require responses. A database 302 is also attached to and managed by the server, which acts as the central repository of data stored and managed by the OIS. A Binary Data Store 318 is also typically attached to the server, which stores additional large pieces of data that are not conveniently stored in the database 302, such as images from an Image Acquisition system. The server can include a Network Interface Device 320 that allows it to communicate to other nodes on the network, including OIS Clients, Imaging Acquisition systems, Treatment Planning systems, and Treatment Delivery systems.

The OIS Client has a processor 308, main memory 306, static memory 310, and ROM 312, as well as a system bus 314 that conveys data among the components of the OIS Client. In an embodiment, the OIS Client may connect to the hospital information system from which the OIS Client may receive information as required. The OIS client has a Network Interface Device 320 through which it communicates to the server. The OIS client typically loads its software over the network, from instructions stored on the server's Drive Unit 316. The OIS client includes components that are utilized by the user interface of the OIS, including a Display device 322 such as an LCD screen, an Alpha-Numeric entry device 324 such as a keyboard, and a cursor control device 326 such as a mouse. Any data that is displayed by the OIS client is requested from the Server over the network 304, and any changes to data made by the OIS client are conveyed to the server to be stored in the Database 302 or in the Binary Data Store 318. Multiple clients can be connected to a single server, and typically multiple Treatment Delivery systems, Image Acquisition systems, and Treatment Planning systems can also be connected to a single server.

In an embodiment, the radiation therapy system may be connected (e.g., networked) to other machines in a Local Area NetWork (LAN), an intranet, an extranet, or the Internet. The machine may operate in the capacity of a server, or a client machine in a client-server network environment, or as a peer machine in a peer-to-peer (or distributed) network environment. The machine may be a personal computer (PC), a tablet (e.g., an iPad, a Microsoft surface tablet, and the like), a Personal Digital Assistant (PDA), a cellular telephone (e.g., an iPhone, and the like), or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In further embodiments, a central server and multiple parallel workstations maybe connected via a network.

In an embodiment, depending on the configuration at a particular hospital, the OIS system may include a system such as illustrated by FIG. 3A.

The radiation therapy system can include a processor, a main memory (e.g., read-only memory (ROM), flash memory, dynamic random access memory (DRAM) such as synchronous DRAM (SDRAM) or Rambus DRAM (RDRAM and the like)), a static memory (e.g., flash memory, static random access memory (SRAM and the like)), and may, in another embodiment, include a secondary memory (e.g., a data storage device such as a memory cache) which communicates with the processor, static memory and main memory via a bus. In accordance with an embodiment, the main memory stores computer-executable instructions corresponding to a plurality of tasks. These computer-executable instructions are executed by the processor. Furthermore, cached memory may be pre-formatted to increase the speed of data loading.

In one embodiment, the memory may be a machine readable storage medium. While the machine-readable storage medium, as an exemplary embodiment, may be a single medium, the term "machine-readable storage medium" should be taken to include a single medium or multiple media (e. g., a centralized or distributed database, and/or associated caches and servers) that store one or more sets of instructions. The term "machine-readable storage medium" shall also be taken to include any medium that is capable of storing or encoding a set of instructions that may lead the machine to perform any one or more of the methodologies of the present invention. The term "machine readable storage medium" shall accordingly be taken to include, but not be limited to, solid-state memories, and optical and magnetic media.

The processor represents one or more general-purpose processing devices such as a microprocessor, central processing unit, or the like. In particular, the processor may be a complex instruction set computing (CISC) microprocessor, reduced instruction set computing (RISC) microprocessor, very long instruction word (VLIW) microprocessor, a processor implementing other instruction sets, or processors implementing a combination of instruction sets. Processor 402 may also be one or more special-purpose processing devices such as an application specific integrated circuit (ASIC), a field programmable gate array (FPGA), a digital signal processor (DSP), network processor, a system on a chip (SoC), or the like. As will be appreciated by those skilled in the art, in some alternative embodiments, the processor may be a special-purpose processor, rather than a general-purpose processor.

As used herein, the term "microcontroller" may include any processor-based or microprocessor-based system including systems using computers, reduced instruction set circuits (RISC), application specific integrated circuits (ASICs), general purpose processor, logic circuits processor, and any other circuit or processor capable of executing the functions described herein. The above are examples only, and are thus not intended to limit in any way the definition and/or meaning of the term "microcontroller".

The set of instructions may include various commands that instruct the processing machine to perform specific operations, such as the processes of the various embodiments of the invention. The set of instructions may be in the form of a software program. The software may be in various forms such as system software or application software. Furthermore, the software may be in the form of a collection of separate programs, a program module within a larger program, or a portion of a program module. The software also may include modular programming in the form of object-oriented programming. The processing of input data by the processing machine may be in response to user commands, or in response to results of previous processing, or in response to a request made by another processing machine.

The processing machine (e.g., processor, microcontroller, and the like) executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a hard disc drive (HDD) and a compact disc read-only memory (CDROM). The above memory types are exemplary only, and are thus not intending to limit the types of memory usable for storage of a computer program.

The radiation therapy system may include a user interface device, video displays (e.g., liquid crystal displays (LCD) and/or a cathode ray tubes (CRT)), an alphanumeric input device (e.g., a keyboard), and a cursor control device (e.g., a mouse). In an embodiment, the video displays may be one or more screens that can be part of a hand-held communication device, such as a tablet (e.g., an iPad, an Android pad, a Nook, a reading pad, and the like), an emailing device (e.g., a Blackberry), or a cellular phone (e.g., an iPhone, a droid, and the like).

Figure 4A:
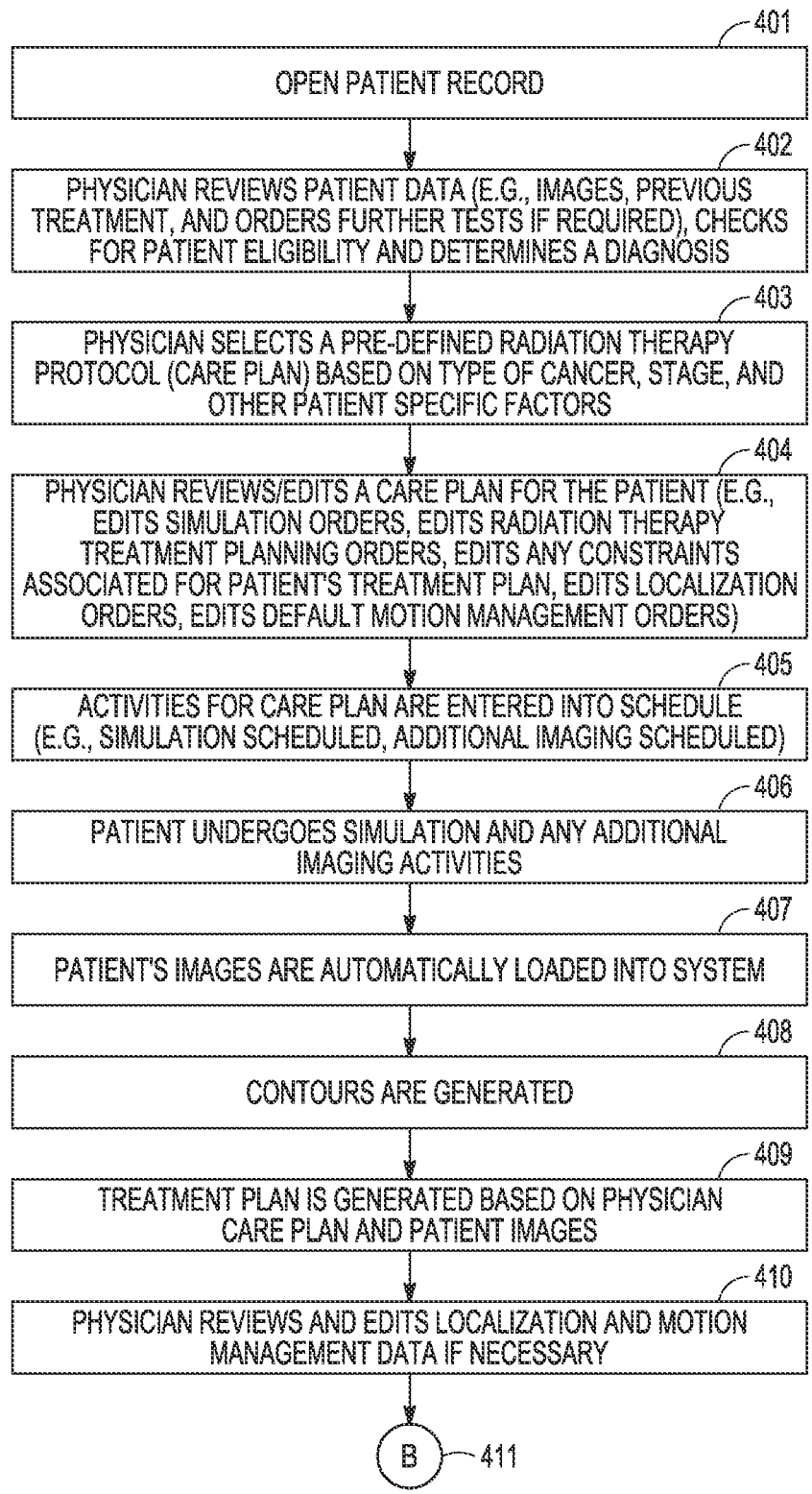
FIGS. 4A, 4B are an example of flow charts of a physician intent module such as can be used in accordance with an embodiment of the present invention.
Figure 4B:
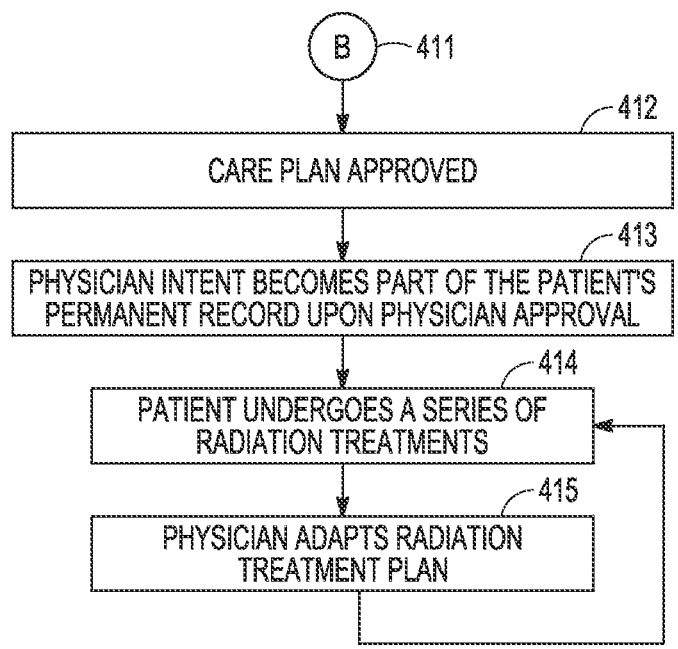

FIG. 4A is an example of a flow chart of a physician intent module such as can be used in accordance with an embodiment of the present invention. At 401, a patient record can be opened, such as by the OIS. Patient data from the patient record can be presented to a physician, e.g., via a display device included in or interfacing with the OIS. At 402, the physician can review the patient data (e.g., images, previous treatment information, etc.) and, using the OIS, can order further tests if desired, can check for patient eligibility for radiation treatment and can determine a diagnosis. Information provided by the physician can be captured and used by the OIS, such as described elsewhere in this document. At 403, the physician can use the OIS to define, specify, or select a pre-defined radiation therapy protocol, which can be included in a computerized initial "patient care plan" (also referred to as a "patient treatment plan") that can be captured and used by the OIS, such as described elsewhere in this document. At 404, the physician can use the OIS to review and/or edit the patient care plan for the patient. This can include, for example, editing simulation orders, editing radiation therapy treatment planning orders, editing any constraints or parameters associated with the patient's treatment plan, editing localization orders, editing default motion management orders, or the like, such as described elsewhere in this document. At 405, activities for the patient care plan are entered by the OIS into the computerized workflow, such as can include a Schedule (e.g., simulation scheduled, additional imaging scheduled, or the like), such as described elsewhere in this document. At 406, the patient can undergo simulation and any additional simulation activities, such as in accordance with the computerized workflow provided or used by the OIS, such as described elsewhere in this document. At 407, any resulting images of the patient can be automatically loaded into the OIS, such for use as described elsewhere in this document. At 408, one or more contours can be generated, such as can define a tumor or other target area to be irradiated. At 409, a patient care plan or patient treatment plan can be generated by the OIS, such as based on the initial patient care plan and adapted according to the contours or other information from the patient images or other relevant information, such as described elsewhere in this document. At 410, the physician can use the OIS to review and/or edit localization and/or Motion Management data or parameters, if desired, such as described elsewhere in this document. At 411, process flow can continue, such as shown in the example of FIG. 4B. FIG. 4B is an example of a flow chart of a physician intent module such as can be used in accordance with an embodiment of the present invention. At 411, process flow can resume, such as where it left of in the example of FIG. 4A. At 412, the patient care plan can be approved, such as by the patient's physician. At 413, the physician intent can be documented by or using the OIS in an initial or adapted patient care plan, which can become a part of the patient's permanent electronic medical record (EMR) or other record, such as upon physician approval. At 414, the patient can undergo one or more radiation treatments, such as can be part of a series or a course of multiple radiation therapy sessions. Resulting information about the delivery or an effect of the radiation treatment can be captured by the OIS, such as described elsewhere in this document. At 415, the OIS can adapt the patient care plan or patient treatment plan, such as can include receiving physician input or approval for adapting the patient care plan or the patient treatment plan.

Figure 5:
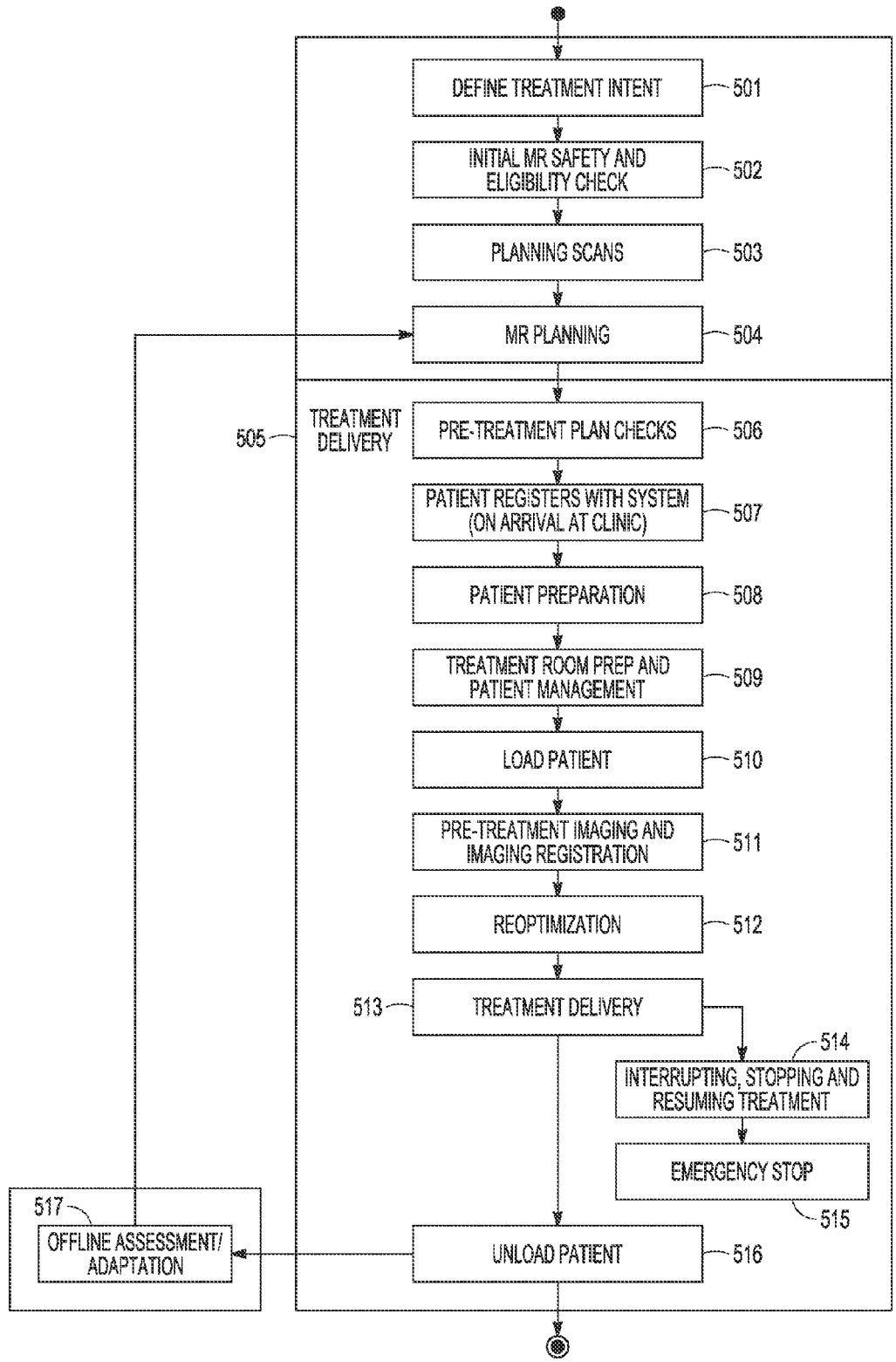
FIG. 5 is an example of a flow chart for a workflow for the OIS.

FIG. 5 is an example of a flow chart for a computerized workflow that can be coordinated using the OIS. At 501, physician input can be received by the OIS, such as for the purpose of defining the physician intent for the computerized initial patient care plan or patient treatment plan being coordinated by the OIS, such as described elsewhere in this document. At 502, an initial MR safety and eligibility check can be performed, and resulting information can be captured and/or used by the OIS, such as described elsewhere in this document. At 503, one or more planning scans can be performed, such as by using an MR scanner to acquire MR imaging information, such as described elsewhere in this document. At 504, the MR imaging information can be used in MR planning such as for assessing the patient's need for radiation therapy and for planning a course of image guided radiation treatment in accordance with an initial or subsequent patient care or treatment plan, such as described elsewhere in this document. At 505, treatment delivery can begin, which can include a series of steps. At 506, one or more pre-treatment plan checks can be performed, information about which can be provided or captured by the OIS, such as described elsewhere in this document. At 507, the patient can register with the OIS, such as upon arrival at the clinic or at the location of the OIS. At 508, patient preparation can be carried out, such as in accordance with any patient preparation instructions provided in the computerized patient care or treatment plan being handled by the OIS. At 509, treatment room preparation and patient management can be carried out, such as in accordance with any instructions provided in the computerized patient care or treatment plan being handled by the OIS. At 510, the patient can be loaded onto the radiation treatment device, such as on a couch of an MR-Linac, such as described elsewhere in this document. At 511, pre-treatment imaging can be performed, such as can include using an MR scanner or other imaging modality. and such immediate pre-treatment images can be registered to planning images of the same patient, or to earlier pre-treatment images acquired after the planning images but acquired before acquisition of the immediate pre-treatment images. At 512, re-optimization of the planned treatment regimen can be carried out by the OIS, such as using information from the immediate pre-treatment images, registration information, patient position information, motion management information, or any other information suitable for re-optimization, such as described elsewhere in this document. At 513, radiation treatment therapy can be carried out, such as by using the MR-Linac device, such as can be controlled by one or more control parameters provided by the OIS in accordance with the computerized initial or adapted patient care plan or the computerized workflow developed therefrom. At 514, if desired, the treatment can include interrupting, stopping, and resuming the treatment. At 515, an emergency stop can be carried out, if needed. At 516, the patient can be unloaded from the radiation treatment apparatus, such as the couch of an MR Linac apparatus. At 517, offline assessment and/or adaptation of the computerized patient care or treatment plan or workflow can be carried out using the OIS, such as described elsewhere in this document. Portions of such assessment can be carried out using the OIS. Physician assessment input can also be received by the OIS at 517. Process flow can than return to 504, such as for further MR planning and subsequent treatment delivery, such as during subsequent radiation therapy sessions in a course of multiple radiation therapy sessions.

Figure 6:
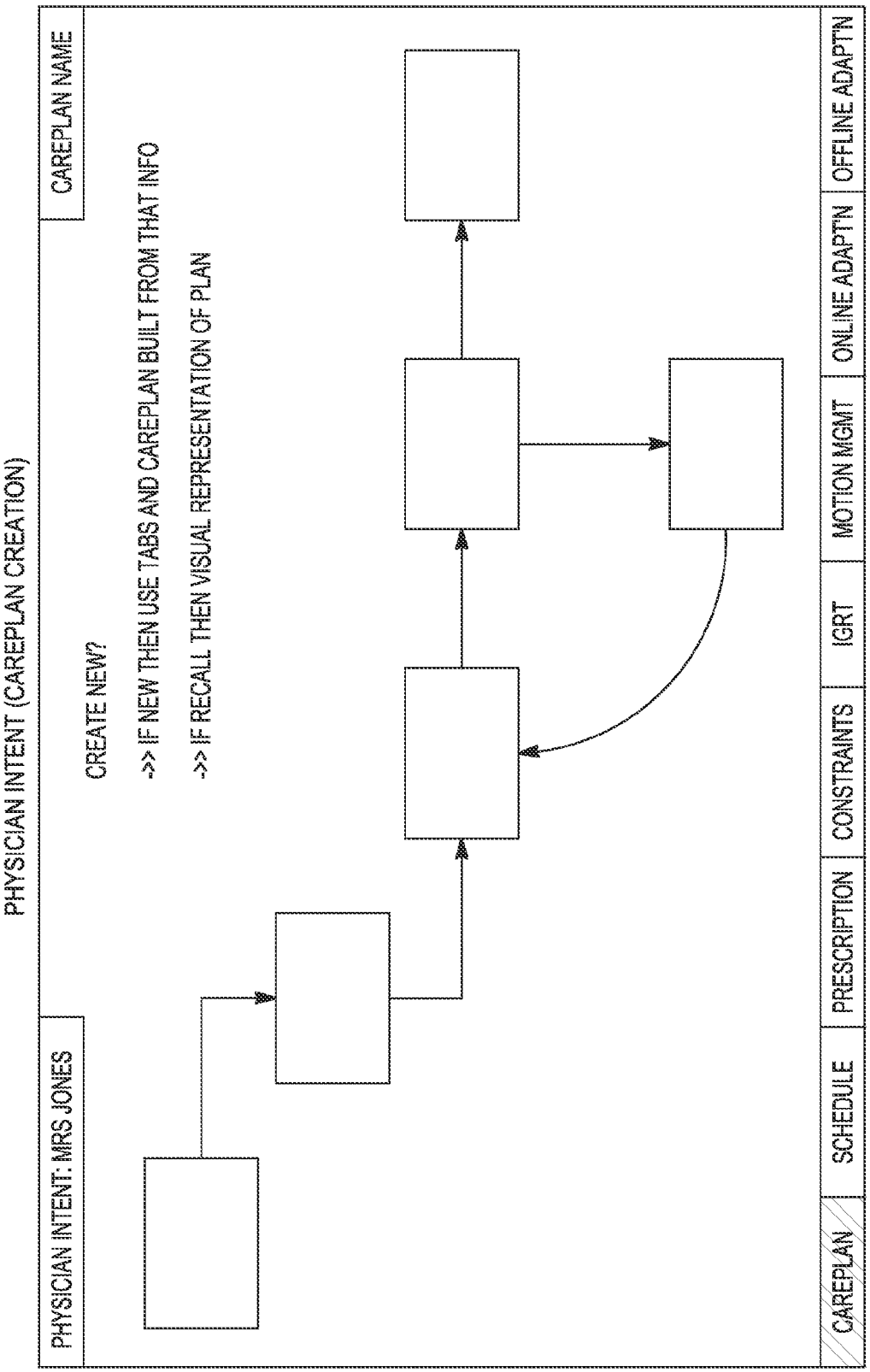

FIG. 6 is an example of a graphical user interface (GUI) such as can be provided on a display of the OIS. FIG. 6 shows a GUI for visualizing and/or facilitating specification of physician intent for creating a patient care or treatment plan. The various elements of the workflow can be illustrated as blocks on the GUI, such as shown in FIG. 6. Various tabs can be provided on the GUI such as to switch between different interface screens being provided by the GUI. In FIG. 6, the "Careplan" tab is selected, resulting in the display of the various blocks illustrating different portions of the patient careplan, such as described elsewhere in this document. The GUI can be interactive, such as to provide data or to receive user input. Other tabs that switch to display of other screens can include, "Schedule," "Prescription," "Constraints," "Image Guided Radiation Therapy (IGRT)," "Motion Management," "Online Adaptation," and/or "Offline Adaptation."

Figure 7:
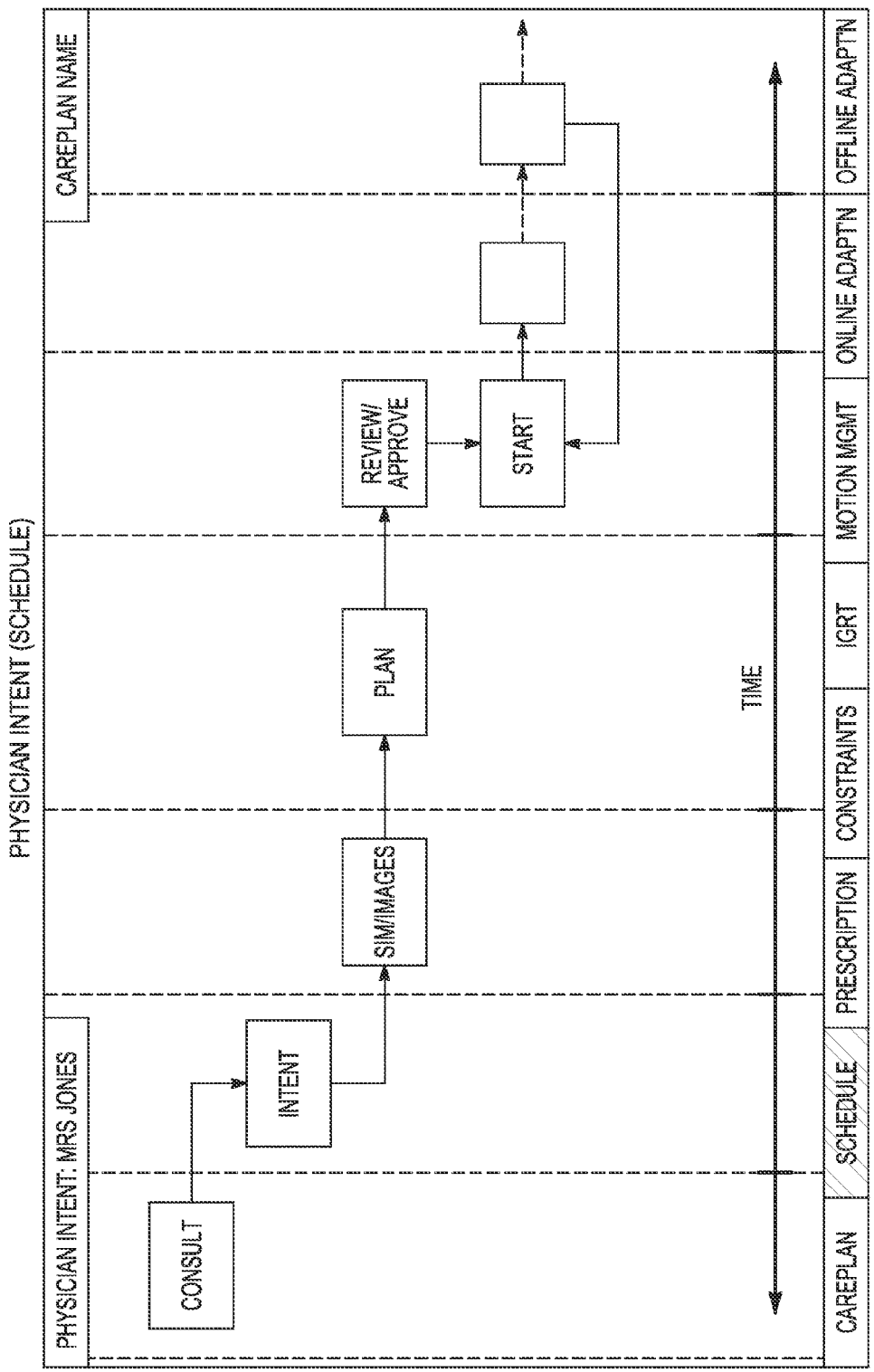

FIG. 7 is an example of the GUI in which a "Schedule" tab has been selected, triggering display of portions of the workflow relevant to scheduling, such as Consult, Intent, Simulation/Images, Treatment Planning, Review/Approval of the patient care or treatment plan, Start of treatment, etc.

FIG. 8 is an example of the GUI in which the radiation therapy Prescription and Constraints tabs have been selected, triggering portions of the workflow, data, or one or more control parameters relevant to each of these. Such information can include Fractionation, CTV Dose, PTV Dose, PTV Margin, PTV Minimum, PTV Maximum, Volume Stats, whether Optimization is required, OAR Maximum Dose constraint, volume under a specified percent of PTV, etc. A graphical (e.g., not limited to alphanumeric) or other visual representation of PTVS based on the prescription can be presented on the GUI, such as can be built dynamically from other information provided to or captured by the OIS.

FIG. 9 is an example of the GUI in which the physician intent with respect to IGRT and Motion Management can be selected via corresponding tabs, triggering portions of the workflow, data, or one or more control parameters relevant to each of these. Such information can include information about Imaging Before Treatment and information about Imaging During Treatment. Examples of information that can be displayed can include: registration tool (e.g., rigid vs. deformable registration), virtual couch shift, dose prediction, Quality Assurance (QA) plan check, reoptimization or other parameters. IGRT parameters can include 1D Navigator, 2D Single plane, 2 planes, 3 planes, orthogonal, parallel, en face, combination 1D and 2D, gating, and/or tracking information. Gating window information e.g., spatial and/or temporal, can be provided. More details about such information is described elsewhere in this document.

Figure 10:
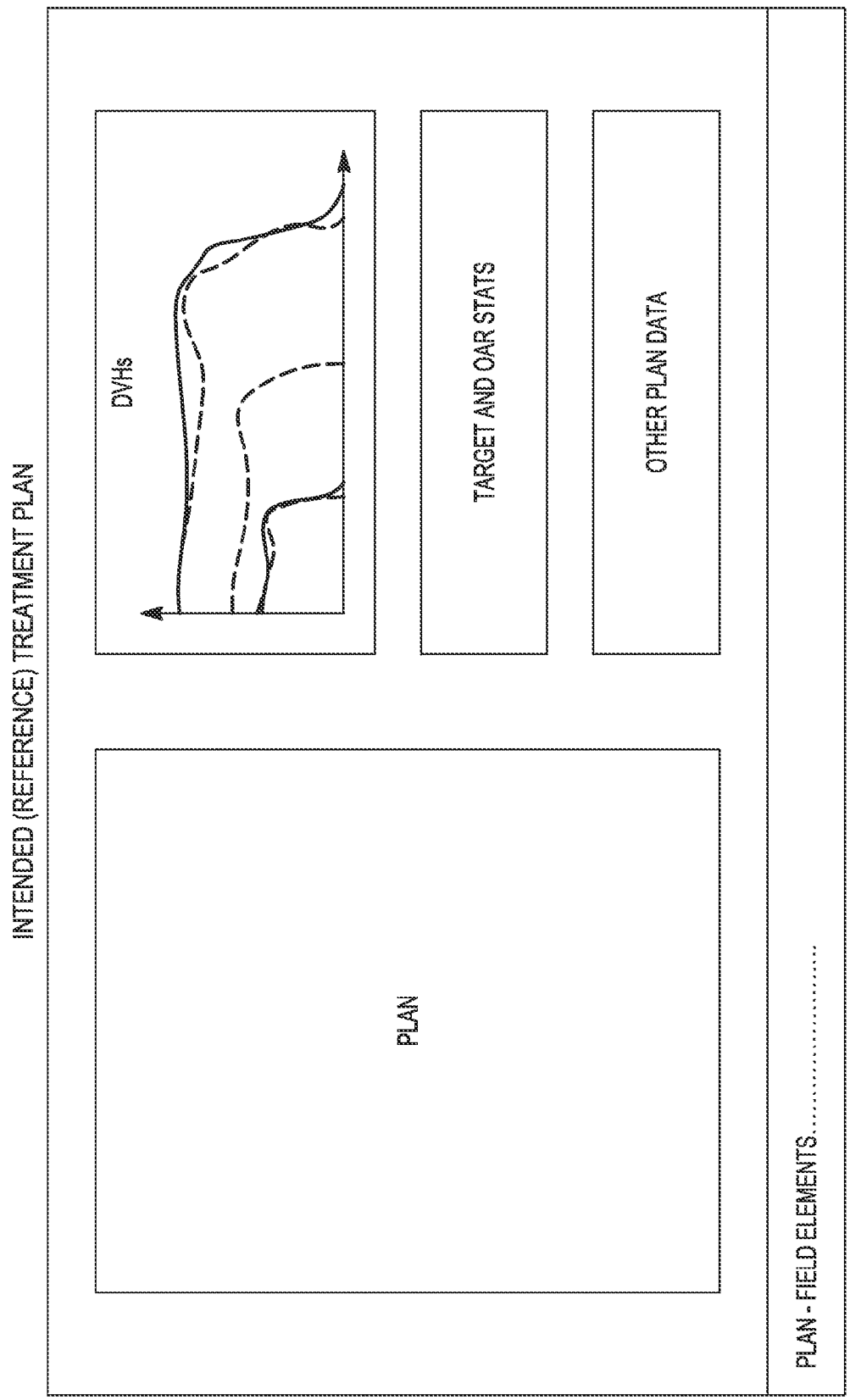

FIG. 10 shows an example of a GUI display that can show information about an intended (e.g., reference) patient care or treatment plan, such as can be displayed together with DVHs, target and OAR statistics, and/or other plan data, such as described elsewhere in this document.

FIG. 11 shows an example of a GUI display that can show information about the intended (e.g., reference) patient care or treatment plan that can be used to establish a tracking window, in this illustrative example, for a conformal lung arc in which tracking can modulate on gantry speed and dose value. Transverse, sagittal, coronal, and en face view gating angle can be displayed, along with selectable parameters such as Show CTV/PTV, Show OAR1, Show OAR2, Track Continuously, Track to within "X" of OAR, Track on Phase, Gate Off Phases, etc.

Figure 12:
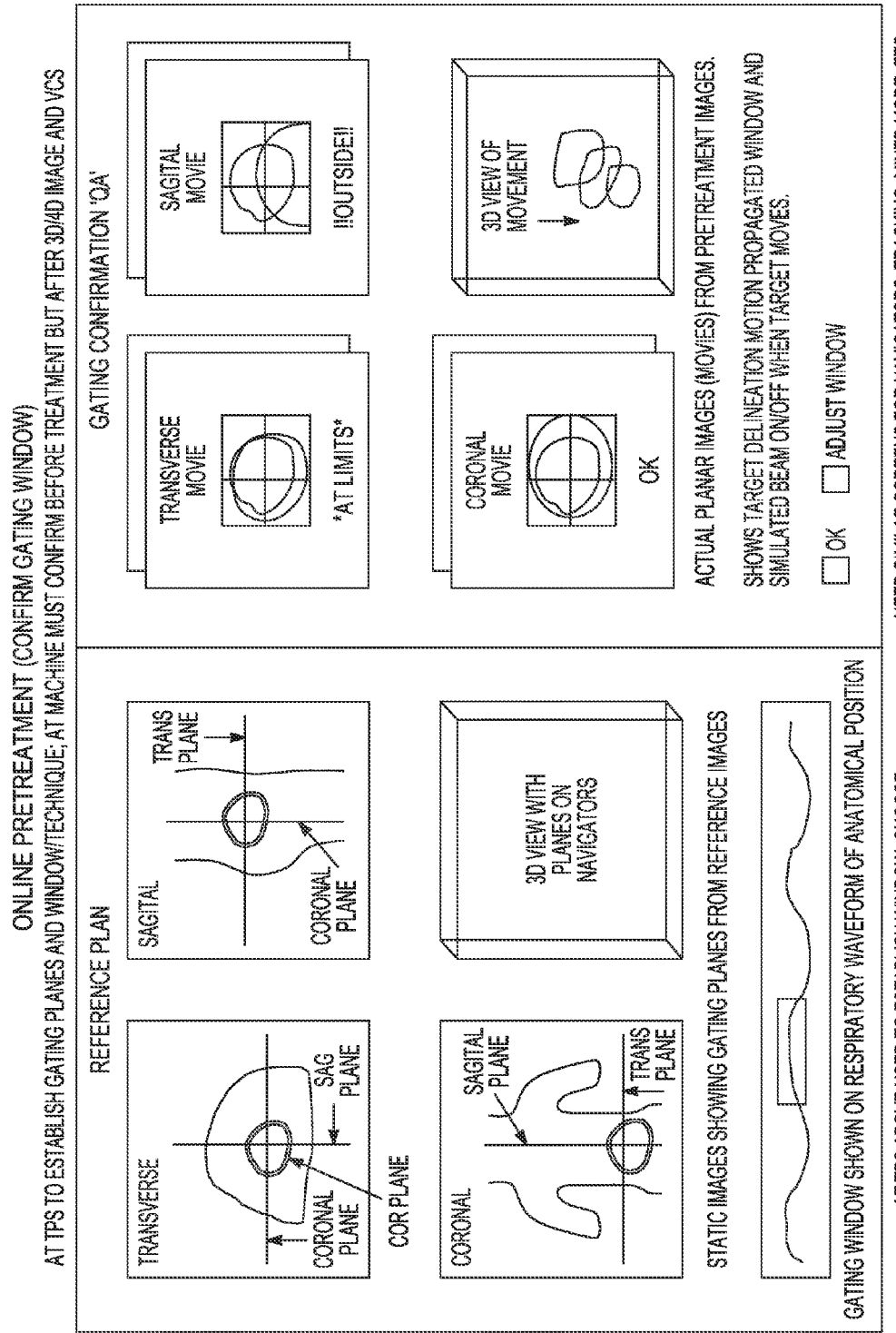

FIG. 12 shows an example of a GUI display that can provide information about Online Pretreatment, such as for confirming the gating window to be used during the actual delivery of radiation therapy. Information about a Reference Plan and Gating Confirmation QA can be provided. The Reference Plan information can include transverse, sagittal, and coronal imaging views, 3D View with planes on Navigators, and Static images showing gating planes from reference images. The Gating Confirmation QA can include a transverse movie, a sagittal movie, a coronal movie, and/or a 3D view of movement, from any or all of which, an assessment of gating or other motion management can be made before actually beginning to deliver the radiation therapy.

Figure 13:
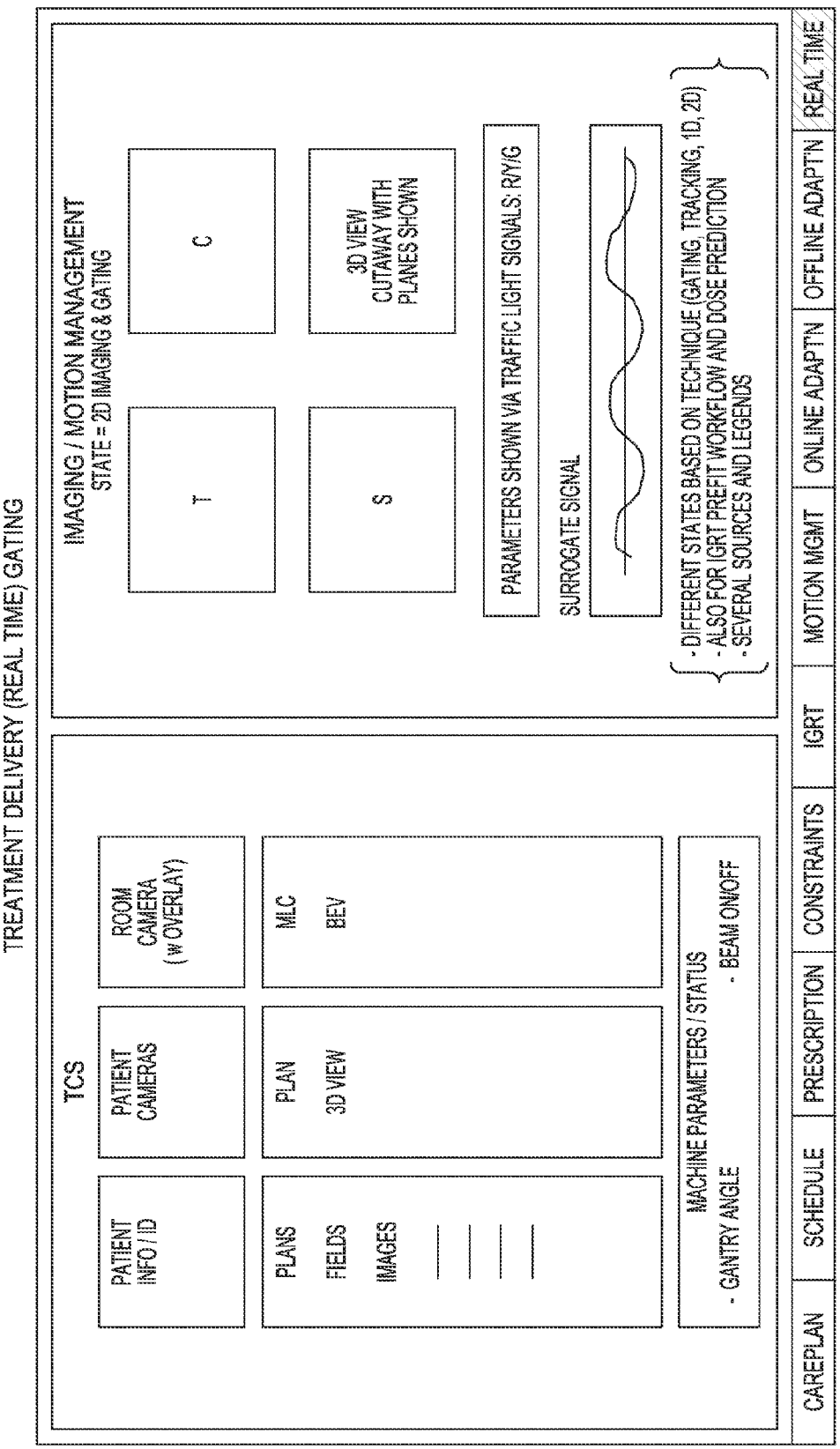
Figure 14:
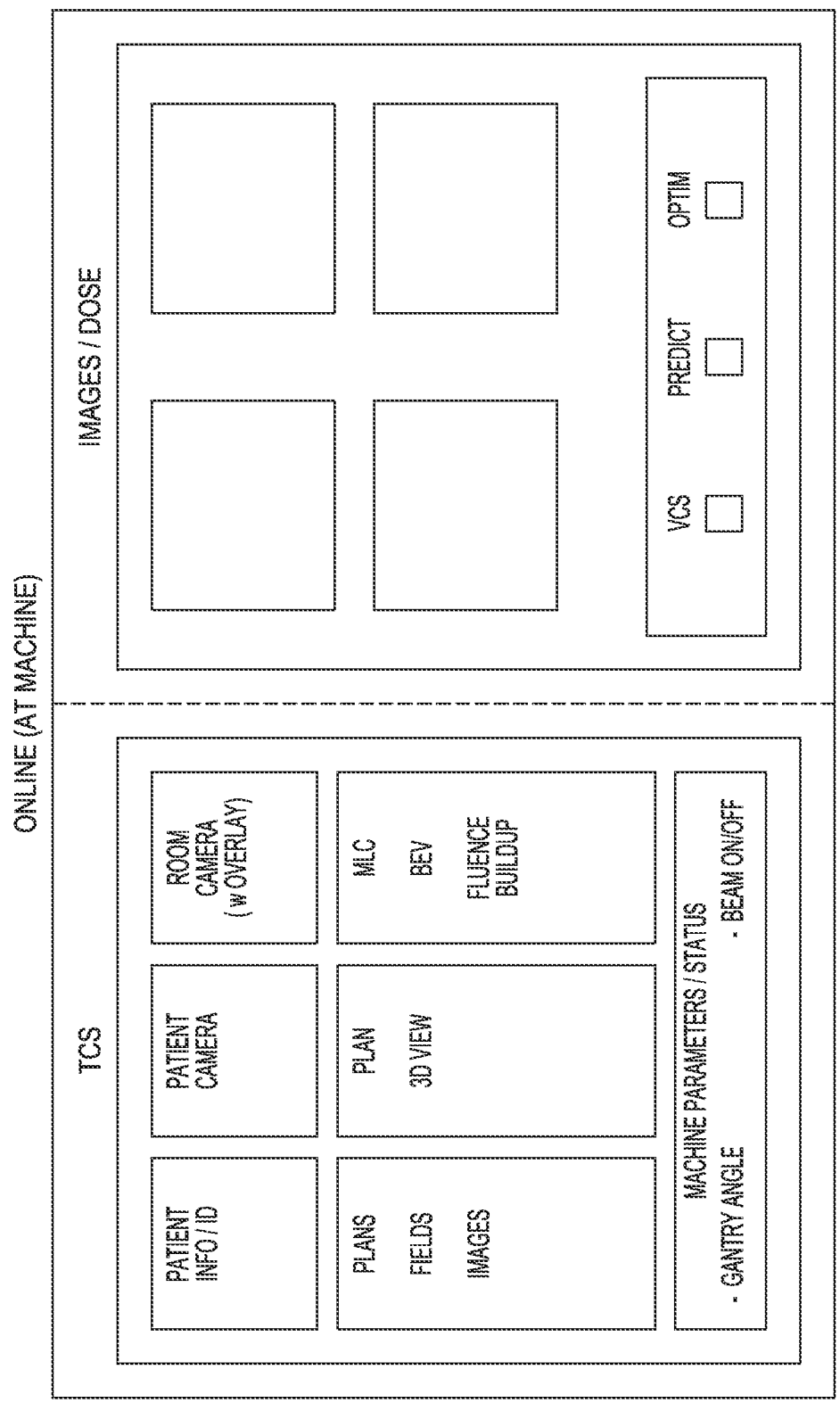

FIGS. 13-14 show examples of a GUI display that can provide information about treatment delivery (e.g., real-time) gating. Displayed information can include patient information/identification, patient camera image, room camera image, plans, fields, images, plan 3D view, multi leaf collimator (MLC) and Beams Eye View (BEV) information, machine parameters and/or status information, such as gantry angle and beam on/off indications. Imaging/Motion Management information displayed can include transverse, sagittal, coronal, and 3D views, parameters shown such as using traffic light (red/yellow/green) type indicators), and a surrogate signal.

Figure 15:
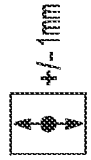

FIG. 15 shows an example of a GUI display that can provide or capture information about offline/online adaptive intent, such as can include Review Frequency, Review Items (e.g., Images, Dose Delivered, Cumulative Dose Delivered, Plan Quality (Target+OAR stats), Plan Quality (DVH differences), Target Changes, or the like. Parameters for guiding replanning or additional image acquisition can also be displayed, such as for capturing user input. Types of Imaging that can be specified via the GUI can include, for example, PET, MR, CT, Volumetric Imaging before Treatment, 3D, 4D, 2D imaging before treatment for gating setup, Verification, 1D navigator such as to establish respiratory traces/target motion, or to set target movement threshold around the Navigator intersection, or to Gate on 2D planes target edge, 1D respiratory pattern on Navigator Pseudo Beacon, or the like.

Figure 16:
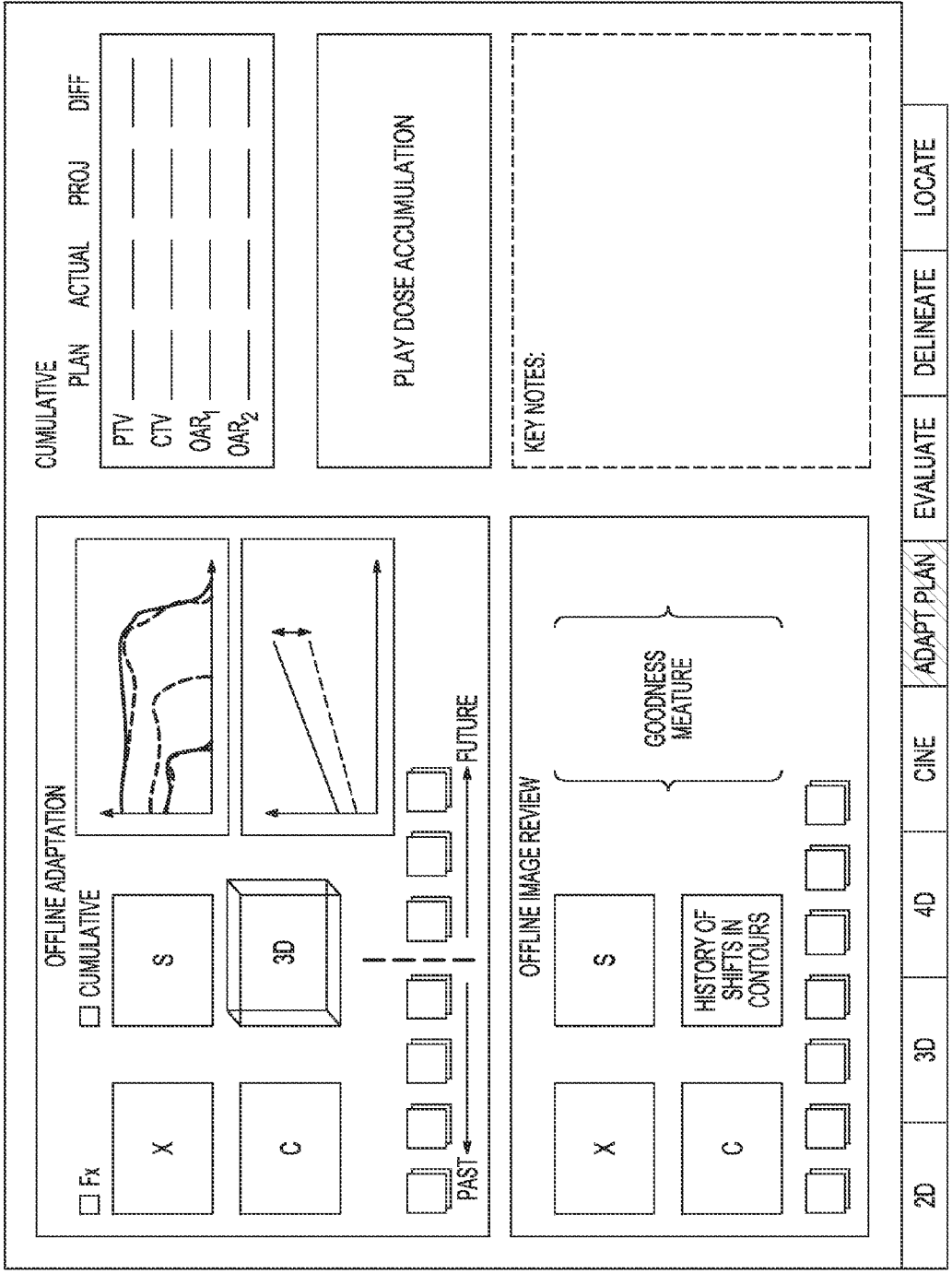

FIG. 16 shows an example of a GUI display such as can be used with the Offline Review to provide an Adaptation Workspace for the user. Fractional and cumulative dose information (e.g., target, OAR, etc.) can be provided to the user, such as for a given treatment session in the course of the multiple treatment sessions. Offline image review information can be provided, such as transverse, sagittal, and coronal views, a history of shifts in contours (e.g., target or OAR).

Figure 17:
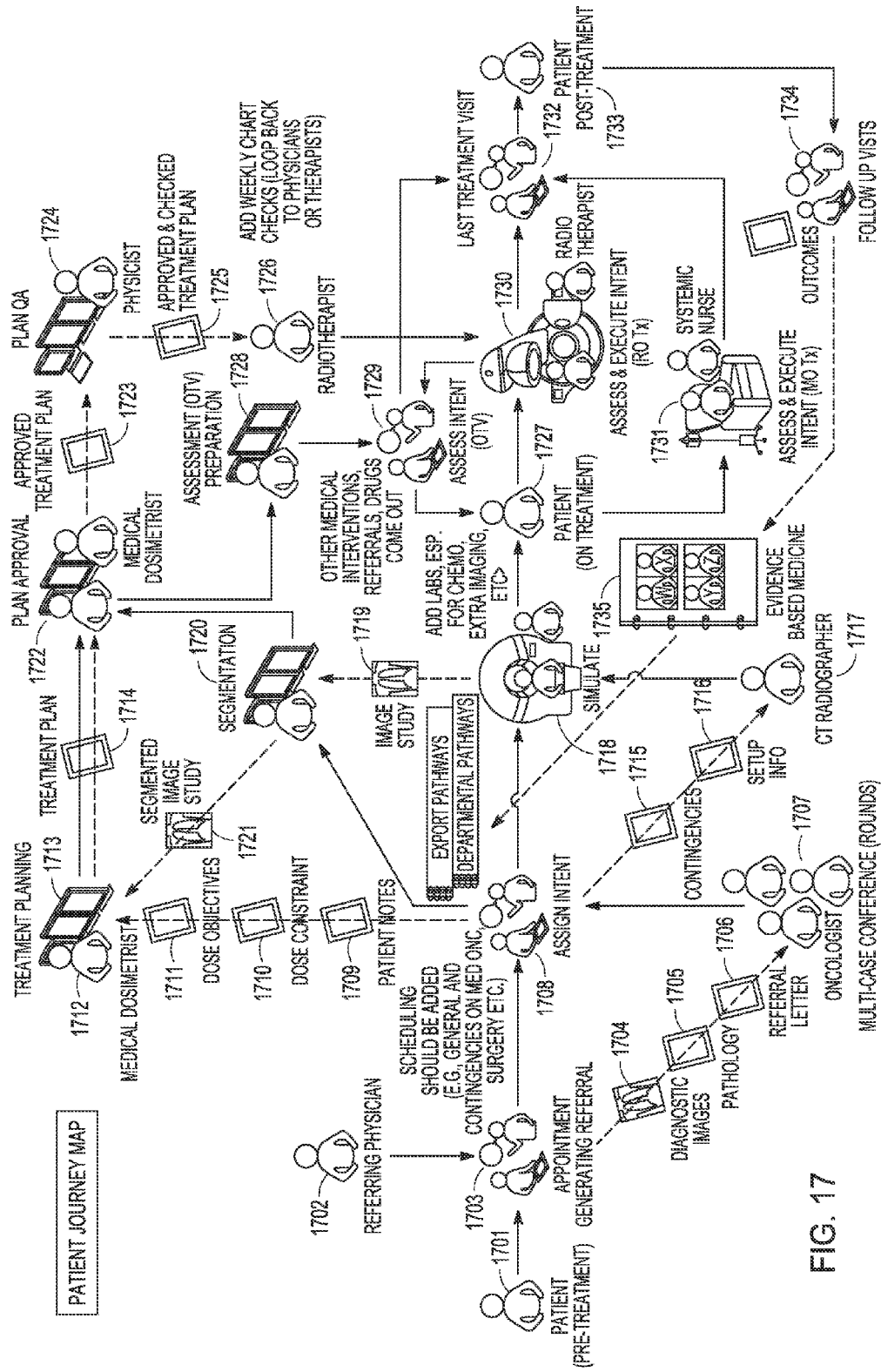
FIG. 17 illustrates an example of a patient journey map, illustrating components included in or interfacing with an embodiment of the present OIS, such as in accordance with a computerized workflow that can be managed by the OIS.

FIG. 17 illustrates an example of a patient journey map, illustrating components included in or interfacing with an embodiment of the present OIS, such as in accordance with a computerized workflow that can be managed by the OIS. In FIG. 17, a patient is shown at 1701, and a referring physician is shown at 1702. At 1703, the patient can meet with the referring physician, such as in an appointment that generates a referral for radiation treatment therapy. Information used or generated during the appointment (e.g., diagnostic images 1704, pathology information 1705, referral letter 1706, or the like) can be communicated using the OIS to a specialist physician, such as a radiation oncologist 1707, who can optionally use the OIS to review such case information with one or more colleagues, such as during a multi-case conference (rounds) before meeting with the patient at 1708 at an appointment during which the radiation oncologist can assign intent ("physician intent") for radiation treatment therapy, which may involve a course of multiple radiation therapy sessions, such as described elsewhere in this document. The OIS can convey such physician intent or other information (e.g., patient notes 1709, dose constraints 1710, dose objectives 1711) to a medical dosimetrist 1712, who can optionally access the OIS remotely from a remote client user interface 1713 of the OIS. The medical dosimetrist can input radiation dose inputs as part of a patient care or treatment plan 1714 that can be hosted and managed by the OIS. Information from the physician intent appointment at 1708 (e.g., contingencies 1715, setup information 1716 or the like) can also be provided via the OIS to a CT radiographer 1717, such as for use during an imaging and simulation session 1718 of the patient. A resulting image study 1719 can be provided by the OIS to a user for a computerized image segmentation session 1720, such as for identifying the tumor or other target to be treated, or for identifying one or more organs at risk (OARs), or both, such as described elsewhere in this document. Based on the segmentation session 1720, resulting segmented image study information 1721 can be provided to the medical dosimetrist, such as for use in establishing the patient care or treatment plan 1714 being hosted by the OIS.

A remote client or other user interface of the OIS can be used by the medical dosimetrist for patient care or treatment plan approval at 1722, such as at a time that is closer to the initiation of course of multiple radiation therapy sessions, or during the course of multiple radiation therapy sessions. The approved patient care or treatment plan 1723 can be provided via the OIS to a medical physicist 1724 such as for performing quality assurance (QA) before or during the course of the multiple therapy sessions. An approved patient care or treatment plan 1725 can be provided via the OIS from the QA medical physicist to a radiotherapist 1726, such as for use during the course of the multiple radiation therapy treatment sessions.

During the course of the multiple treatment sessions, the patient can appear at 1727 for a particular treatment session, such as can be facilitated by the OIS. The approved patient care or treatment plan can be provided, via the OIS for pre-treatment patient assessment at 1728. The patient assessment at 1728 can be coupled with an assessment at 1729 of then-existing patient information against the previously specified physician intent. After such pre-treatment assessment, the patient can undergo a treatment session, such as an image-guided radiotherapy treatment session at 1730 (e.g., using an MR-Linac device) under supervision of the radiotherapist. A particular treatment session can additionally or alternatively include a non-radiation-therapy treatment session at 1731, such as chemotherapy or systemic therapy that can be provided by a systemic nurse or internist. Similarly, the patient can appear for subsequent treatment sessions in the series of treatment sessions, between which re-assessment of the patient (e.g., comparing progress of the treatment against the physician intent) at 1729 can be carried out using the OIS offline, such as described elsewhere in this document. Upon completion of the series of multiple radiation therapy sessions at 1732 the post-treatment patient 1733 can be followed up during one or more follow-up visits at 1734. Information about the particulars of the radiation therapy treatment sessions and their effect or efficacy can be processed into an evidence based medicine database 1735, such as for use by the physician in the physician intent assignment appointments for the same or other patients at 1708, or elsewhere.

Additional Notes

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Example 1 can include or use subject matter (such as an apparatus, a method, a means for performing acts, or a device readable medium including instructions that, when performed by the device, can cause the device to perform acts, such as can include or use: obtaining computerized physician intent data representing an initial patient care plan for a patient; creating a computerized workflow for the patient to include a course of multiple radiation therapy sessions; performing a plurality of computer-executable instructions on a processor circuit of the oncology computer system to generate a plurality of control parameters for a radiation therapy apparatus to provide the radiation treatment to a patient in accordance with the workflow during the course of the multiple radiation therapy sessions; obtaining computerized treatment data after initiating the course of the multiple radiation therapy sessions; processing the computerized treatment data, using the processor circuit, to determine an indication of delivery or effect of the radiation treatment during the course of the multiple radiation therapy sessions based on the initial patient care plan relative to the workflow; using the indication of delivery or effect of the radiation treatment to adapt the patient care plan; and managing the workflow for the patient using the adapted patient care plan as the patient proceeds through a course of multiple radiation therapy sessions.

Example 2 can include, or can optionally be combined with the subject matter of Example 1, to optionally include obtaining computerized Physician Intent data comprising combining at least two of: (1) treatment simulation data; (2) patient imaging data; (3) patient treatment planning information; (4) patient motion management data; (5) patient registration data; (6) localization definition or frequency data; (7) adaptive planning data; and (8) one or more specified triggers.

Example 3 can include, or can optionally be combined with the subject matter of one or any combination of Examples 1 or 2, to optionally include adapting the patient care plan, comprising: using the processor circuit, processing the computerized Physician Intent data; determining an indication of a deviation from the initial or a current patient care plan; and adapting one or more subsequent radiation therapy sessions specified in the patient care plan based on the indication of the deviation from the initial or the current patient care plan.

Example 4 can include, or can optionally be combined with the subject matter of one or any combination of Examples 1 through 3, to optionally include the current patient care plan being previously adapted at least one time during the course of multiple radiation therapy sessions.

Example 5 can include, or can optionally be combined with the subject matter of one or any combination of Examples 1 through 4, to optionally include managing a workflow for a patient based on the adapted patient care plan, comprising: performing a plurality of computer-executable instructions on a processor circuit of the oncology computer system to process the physician intent data to manage at least one of a simulation activity, a planning adaptation activity, a motion management activity, an imaging protocol, or a localization activity, or to verify that a predetermined protocol is followed.

Example 6 can include, or can optionally be combined with the subject matter of one or any combination of Examples 1 through 5, to optionally include wherein using the indication of delivery or effect of the radiation treatment to adapt the patient care plan comprises adapting at least one of a treatment review schedule or treatment re-planning schedule based on the indication of delivery or effect of the radiation treatment.

Example 7 can include, or can optionally be combined with the subject matter of one or any combination of Examples 1 through 6, to optionally include wherein using the indication for delivery or effect of the radiation treatment to adapt the patient care plan comprises determining an actual radiation dose received by the patient for a particular radiation therapy session.

Example 8 can include, or can optionally be combined with the subject matter of one or any combination of Examples 1 through 7, to optionally include wherein using the indication for delivery or effect of the radiation treatment to adapt the patient care plan comprises determining an accumulated radiation dose of all dosages previously received by the patient during the course of the multiple therapy sessions.

Example 9 can include, or can optionally be combined with the subject matter of one or any combination of Examples 1 through 8, to optionally include wherein using the indication of delivery or effect of the radiation treatment to adapt the patient care plan during the course of the multiple radiation therapy sessions comprises adapting a patient motion management parameter based on the indication of delivery or effect of the radiation treatment.

Example 10 can include, or can optionally be combined with the subject matter of one or any combination of Examples 1 through 9, to optionally include wherein the processing the computerized treatment data, using the processor circuit, to determine an indication of delivery or effect of the radiation treatment comprises determining an efficacy of the delivery of the radiation treatment during at least one of the multiple radiation therapy sessions.

Example 11 can include, or can optionally be combined with the subject matter of one or any combination of Examples 1 through 10, to optionally include wherein the determining an efficacy of the delivery of the radiation treatment comprises: comparing the treatment data for one or more of the multiple radiation therapy sessions to data from a patient population of other patients that is stored in a database; comparing the treatment data against one or more triggers specified in the physician intent data; and generating a predictive alert and presenting it to a user based on a result of the comparison.

Example 12 can include, or can optionally be combined with the subject matter of one or any combination of Examples 1 through 11, to optionally include wherein the predictive alert includes at least one of: a high dose or low dose alert; a dose volume histogram (DVH) alert; a fractional biologically effective dose (BED) alert; a percentage or absolute volume deviation alert; a change in tumor control probability (TCP) alert; a normal tissue complication probability (NTCP) alert; and a change in region of interest alert.

Example 13 can include, or can optionally be combined with the subject matter of one or any combination of Examples 1 through 12, to optionally include wherein managing a workflow for a patient comprises: using the predictive alert to adapt the patient care plan as the patient proceeds through the course of multiple radiation therapy sessions; and notifying a user to a change in the patient care plan.

Example 14 can include, or can optionally be combined with the subject matter of one or any combination of Examples 1 through 13, to optionally include wherein notifying a user to a change in the patient care plan comprises generating at least one of a notification for a user error, a treatment error, or a treatment deviation.

Example 15 can include, or can optionally be combined with the subject matter of one or any combination of Examples 1 through 14, to optionally include displaying, on a computer display, a visualization of a tumor target in the patient and a visualization of a radiation dose delivered to the tumor target in the patient.

Example 16 can include, or can optionally be combined with the subject matter of one or any combination of Examples 1 through 15, to optionally include displaying, on a computer display, a visualization of a non-target organ at risk (OAR) and of a radiation dose delivered to the non-target OAR.

Example 17 can include, or can optionally be combined with the subject matter of one or any combination of Examples 1 through 16, to optionally include obtaining patient imaging data including (1) planning imaging data of the patient, (2) therapy session imaging data of the patient, or (3) rigid or deformable registration information between the planning imaging data of the patient and the therapy session imaging data of the patient.

Example 18 can include, or can optionally be combined with the subject matter of one or any combination of Examples 1 through 17, to optionally include determining at least one of: dose data; dose volume histogram (DVH) data; fractional biologically effective dose data; tumor control probability (TCP) data; normal tissue complication probability (NTCP) data; and region of interest volume data.

Example 19 can include, or can optionally be combined with the subject matter of one or any combination of Examples 1 through 18, to optionally include determining predictive trend information of at least one predictive trend including at least one of: a dose data trend; a fractional biologically effective dose data trend; a tumor control probability (TCP) data trend; a normal tissue complication probability (NTCP) data trend; a dose volume histogram (DVH) trend; a dose isocontours trend; and a region of interest trend.

Example 20 can include, or can optionally be combined with the subject matter of one or any combination of Examples 1 through 19, to optionally include using the predictive trend information with the initial or adapted patient care plan to predict at least one subsequent course of radiation therapy.

Example 21 can include, or can optionally be combined with the subject matter of one or any combination of Examples 1 through 20, to optionally include using the predictive trend information with the initial or adapted treatment plan to trigger a notification of at least one of a user error, a treatment error, or a treatment deviation.

Example 22 can include, or can optionally be combined with the subject matter of one or any combination of Examples 1 through 21, to optionally include wherein managing the workflow comprises monitoring an quality assurance indication about a delivery of a pre-determined radiation dose to a patient in accordance with the initial patient care plan relative to any adaptation to the initial patient care plan.

Example 23 can include, or can optionally be combined with the subject matter of one or any combination of Examples 1 through 22, to optionally include wherein a radiation therapy session includes one or more fractions of a course of radiation therapy.

Example 24 can include or use subject matter (such as a system, an apparatus, a method, a means for performing acts, or a device readable medium including instructions that, when performed by the device, can cause the device to perform acts, such as can include or use, or can optionally be combined with the subject matter of one or any combination of Examples 1 through 23, to optionally include or use a computer-implemented adaptive radiation therapy management system, comprising: an oncology computer that interfaces with a storage device that stores a plurality of clinical data and patient images, wherein the oncology computer includes a processor circuit that includes or interfaces with at least one of: a physician intent module, configured to provide physician intent data representing a computerized initial patient care plan for a patient who is to undergo radiation treatment during a course of multiple radiation therapy sessions; an off-line review module, configured to allow review the initial or an adapted patient care plan off-line during the course of multiple radiation therapy sessions; and a predictive intent module, configured to initial the patient care plan; and wherein the physician intent module interfaces with the off-line review module and the predictive intent module to manage a computerized workflow for the patient as the patient proceeds through a course of multiple radiation therapy sessions.

Example 25 can include, or can optionally be combined with the subject matter of one or any combination of Examples 1 through 24, to optionally include wherein the physician intent module specifies one or more triggers and specifies one or more tolerances and provides one or more user-notifications in substantially real-time of a predicted or actual deviation from the initial or an adapted patient care plan.

Example 26 can include, or can optionally be combined with the subject matter of one or any combination of Examples 1 through 25, to optionally include wherein the physician intent module determines the initial patient care plan by combining at least two of: (1) treatment simulation data; (2) patient imaging data; (3) patient treatment planning information; (4) patient motion management data; (5) patient registration data; (6) localization definition or frequency data; (7) adaptive planning data; and (8) one or more specified triggers.

Example 27 can include, or can optionally be combined with the subject matter of one or any combination of Examples 1 through 26, to optionally include the processor circuit being configured to perform a plurality of computer-executable instructions to: determine an indication of deviation from the initial or a current patient care plan; and adapt one or more subsequent sessions specified in the patient care plan based on the indication of the deviation from the initial or the current patient care plan.

Example 28 can include, or can optionally be combined with the subject matter of one or any combination of Examples 1 through 27, to optionally include the processor circuit being configured to perform a plurality of computer-executable instructions to process the physician intent data to manage the computerized workflow for the patient to manage at least one of a simulation activity, a planning adaptation activity, a motion management activity, an imaging protocol, or a localization activity, or to verify that a predetermined protocol is followed.

Example 29 can include, or can optionally be combined with the subject matter of one or any combination of Examples 1 through 28, to optionally include the processor circuit being configured to perform a plurality of computer-executable instructions to use an indication of delivery or effect of the radiation treatment to adapt the patient care plan.

Example 30 can include, or can optionally be combined with the subject matter of one or any combination of Examples 1 through 29, to optionally include the processor circuit being configured to perform a plurality of computer-executable instructions to use an indication of delivery or effect of the radiation treatment to adapt the patient care plan, including adapting at least one of a treatment review schedule or treatment re-planning schedule based on the indication of delivery or effect of the radiation treatment.

Example 31 can include, or can optionally be combined with the subject matter of one or any combination of Examples 1 through 30, to optionally include the processor circuit being configured to perform a plurality of computer-executable instructions to adapt the patient care plan using a determination of an actual radiation dose received by the patient for a particular radiation therapy session.

Example 32 can include, or can optionally be combined with the subject matter of one or any combination of Examples 1 through 31, to optionally include the processor circuit being configured to perform a plurality of computer-executable instructions to adapt the patient care plan using a determination of an accumulated radiation dose of all dosages previously received by the patient during the course of the multiple therapy sessions.

Example 33 can include, or can optionally be combined with the subject matter of one or any combination of Examples 1 through 32, to optionally include the processor circuit being configured to perform a plurality of computer-executable instructions to adapt a patient motion management parameter based on an indication of delivery or effect of the radiation treatment.

Example 34 can include, or can optionally be combined with the subject matter of one or any combination of Examples 1 through 33, to optionally include the processor circuit being configured to perform a plurality of computer-executable instructions to adapt the patient care plan using a determination of an efficacy of the delivery of the radiation treatment during at least one of the multiple radiation therapy sessions.

Example 35 can include, or can optionally be combined with the subject matter of one or any combination of Examples 1 through 34, to optionally include the processor circuit being configured to perform a plurality of computer-executable instructions to: compare the treatment data for one or more of the multiple radiation therapy sessions to data from a patient population of other patients that is stored in a database; compare the treatment data against one or more triggers specified in the physician intent data; and generate a predictive alert and present it to a user based on a result of the comparison.

Example 36 can include, or can optionally be combined with the subject matter of one or any combination of Examples 1 through 35, to optionally include the predictive alert including at least one of: a high dose or low dose alert; a dose volume histogram (DVH) alert; a fractional biologically effective dose (BED) alert; a percentage or absolute volume deviation alert; a change in tumor control probability (TCP) alert; a normal tissue complication probability (NTCP) alert; and a change in region of interest alert.

Example 37 can include, or can optionally be combined with the subject matter of one or any combination of Examples 1 through 36, to optionally include the processor circuit being configured to perform a plurality of computer-executable instructions to use the predictive alert to adapt the patient care plan as the patient proceeds through the course of multiple radiation therapy sessions, and to provide a notification to a user to a change in the patient care plan.

Example 38 can include, or can optionally be combined with the subject matter of one or any combination of Examples 1 through 37, to optionally include the notification to the user including at least one of a notification of a user error, a treatment error, or a treatment deviation.

Example 39 can include, or can optionally be combined with the subject matter of one or any combination of Examples 1 through 38, to optionally include or interface with a computer display, and wherein the processor circuit is configured to perform a plurality of computer-executable instructions to display on the computer display a visualization of a tumor target in the patient and a visualization of a radiation dose delivered to the tumor target in the patient.

Example 40 can include, or can optionally be combined with the subject matter of one or any combination of Examples 1 through 39, to optionally include or interface with a computer display, and wherein the processor circuit is configured to perform a plurality of computer-executable instructions to display on the computer display a visualization of a non-target organ at risk (OAR) and of a radiation dose delivered to the non-target OAR.

Example 41 can include, or can optionally be combined with the subject matter of one or any combination of Examples 1 through 40, to optionally include the processor circuit being configured to perform a plurality of computer-executable instructions to obtain patient imaging data including (1) planning imaging data of the patient, (2) therapy session imaging data of the patient, or (3) rigid or deformable registration information between the planning imaging data of the patient and the therapy session imaging data of the patient.

Example 42 can include, or can optionally be combined with the subject matter of one or any combination of Examples 1 through 41, to optionally include the processor circuit being configured to perform a plurality of computer-executable instructions to determine at least one of: dose data; dose volume histogram (DVH) data; fractional biologically effective dose data; tumor control probability (TCP) data; normal tissue complication probability (NTCP) data; and region of interest volume data.

Example 43 can include, or can optionally be combined with the subject matter of one or any combination of Examples 1 through 42, to optionally include the processor circuit being configured to perform a plurality of computer-executable instructions to determine at least one of: a dose data trend; a fractional biologically effective dose data trend; a tumor control probability (TCP) data trend; a normal tissue complication probability (NTCP) data trend; a dose volume histogram (DVH) trend; a dose isocontours trend; and a region of interest trend.

Example 44 can include, or can optionally be combined with the subject matter of one or any combination of Examples 1 through 43, to optionally include the processor circuit being configured to perform a plurality of computer-executable instructions to use the predictive trend information with the initial or adapted patient care plan to predict at least one subsequent course of radiation therapy.

Example 45 can include, or can optionally be combined with the subject matter of one or any combination of Examples 1 through 44, to optionally include wherein the processor circuit is configured to perform a plurality of computer-executable instructions to use the predictive trend information with the initial or adapted treatment plan to trigger a notification of at least one of a user error, a treatment error, or a treatment deviation.

Example 46 can include, or can optionally be combined with the subject matter of one or any combination of Examples 1 through 45, to optionally include the processor circuit being configured to perform a plurality of computer-executable instructions to monitor an quality assurance indication about a delivery of a pre-determined radiation dose to a patient in accordance with the initial patient care plan relative to any adaptation to the initial patient care plan.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

Embodiments of the invention may be implemented with computer-executable instructions. The computer-executable instructions (e.g., software code) may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CDROMS, magnetic-optical disks, removable optical disks (e.g., compact disks and digital video disks), flash memory devices, magnetic cassettes, memory cards or sticks (e.g., secure digital cards), random access memories (RAMs) (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the invention, the method of creating a component or module can be implemented in software, hardware, or a combination thereof. The methods provided by various embodiments of the present invention, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

What is claimed is:

1. A computer-implemented method of facilitating radiation treatment management using a computerized oncology computer system, the method comprising:
    obtaining computerized physician intent data representing an initial patient care plan for a patient;
    creating a computerized workflow for the patient to include a course of multiple radiation therapy sessions;
    performing a plurality of computer-executable instructions on a processor circuit of the oncology computer system to generate a plurality of control parameters for a radiation therapy apparatus to provide the radiation treatment to a patient in accordance with the workflow during the course of the multiple radiation therapy sessions;
    obtaining computerized treatment data after initiating the course of the multiple radiation therapy sessions;
    processing the computerized treatment data, using the processor circuit, to determine an indication of effect on a patient tumor characteristic of the radiation treatment during the course of the multiple radiation therapy sessions based on the initial patient care plan relative to the workflow, including determining, based on the treatment data, an efficacy of the delivery of the radiation treatment during at least one of the multiple radiation therapy sessions, wherein the determining an efficacy of the delivery of the radiation treatment comprises: comparing the treatment data, including patient tumor characteristic data for one or more of the multiple radiation therapy sessions to data, including patient tumor characteristic data from a patient population of other patients that is stored in a database, comparing the treatment data against one or more triggers specified in the physician intent data, and generating a predictive alert and presenting it to a user based on a result of the comparison;
    using the indication of effect on the patient tumor characteristic of the radiation treatment to adapt the patient care plan; and
    managing the workflow for the patient using the adapted patient care plan as the patient proceeds through a course of multiple radiation therapy sessions.

2. The computer-implemented method of claim 1, wherein obtaining computerized Physician Intent data, comprises combining at least two of:
    (1) treatment simulation data;
    (2) patient imaging data;
    (3) patient treatment planning information;
    (4) patient motion management data;
    (5) patient registration data;
    (6) localization definition or frequency data;
    (7) adaptive planning data; and
    (8) one or more specified triggers.

3. The computer-implemented method of claim 1, wherein adapting the patient care plan, comprises:
    using the processor circuit, processing the computerized Physician Intent data;
    determining an indication of a deviation from the initial or a current patient care plan; and
    adapting one or more subsequent radiation therapy sessions specified in the patient care plan based on the indication of the deviation from the initial or the current patient care plan.

4. The computer-implemented method of claim 3, wherein the current patient care plan has been previously adapted at least one time during the course of multiple radiation therapy sessions.

5. The computer-implemented method of claim 1, wherein managing a workflow for a patient based on the adapted patient care plan, comprises:
    performing a plurality of computer-executable instructions on a processor circuit of the oncology computer system to process the physician intent data to manage at least one of a simulation activity, a planning adaptation activity, a motion management activity, an imaging protocol, or a localization activity, or to verify that a predetermined protocol is followed.

6. The computer-implemented method of claim 1, wherein using an indication of delivery or effect of the radiation treatment to adapt the patient care plan comprises adapting at least one of a treatment review schedule or treatment re-planning schedule based on the indication of delivery or effect of the radiation treatment.

7. The computer-implemented method of claim 6, wherein using the indication for delivery or effect of the radiation treatment to adapt the patient care plan comprises determining an actual radiation dose received by the patient for a particular radiation therapy session.

8. The computer-implemented method of claim 6, wherein using the indication for delivery or effect of the radiation treatment to adapt the patient care plan comprises determining an accumulated radiation dose of all dosages previously received by the patient during the course of the multiple therapy sessions.

9. The computer-implemented method of claim 1, wherein using an indication of delivery or effect of the radiation treatment to adapt the patient care plan during the course of the multiple radiation therapy sessions comprises adapting a patient motion management parameter based on the indication of delivery or effect of the radiation treatment.

10. The computer-implemented method of claim 1, wherein the processing the computerized treatment data, using the processor circuit, to determine an indication of delivery or effect of the radiation treatment comprises determining an efficacy of the delivery of the radiation treatment during at least one of the multiple radiation therapy sessions.

11. The computer-implemented method of claim 10, wherein the determining an efficacy of the delivery of the radiation treatment comprises:
    comparing the treatment data for one or more of the multiple radiation therapy sessions to data from a patient population of other patients that is stored in a database;
    comparing the treatment data against one or more triggers specified in the physician intent data; and
    generating a predictive alert and presenting it to a user based on a result of the comparison.

12. The computer-implemented method of claim 11, wherein the predictive alert includes at least one of:
    a high dose or low dose alert;
    a dose volume histogram (DVH) alert;
    a fractional biologically effective dose (BED) alert;
    a percentage or absolute volume deviation alert;
    a change in tumor control probability (TCP) alert;
    a normal tissue complication probability (NTCP) alert; and
    a change in region of interest alert.

13. The computer-implemented method of claim 11, wherein managing a workflow for a patient comprises:
    using the predictive alert to adapt the patient care plan as the patient proceeds through the course of multiple radiation therapy sessions; and
    notifying a user to a change in the patient care plan.

14. The computer-implemented method of claim 13, wherein notifying a user to a change in the patient care plan comprises generating at least one of a notification for a user error, a treatment error, or a treatment deviation.

15. The computer-implemented method of claim 1, comprising:
displaying, on a computer display, a visualization of a tumor target in the patient and a visualization of a radiation dose delivered to the tumor target in the patient.

16. The computer-implemented method of claim 1, comprising:
displaying, on a computer display, a visualization of a non-target organ at risk (OAR) and of a radiation dose delivered to the non-target OAR.

17. The computer-implemented method of claim 1, comprising:
obtaining patient imaging data including (1) planning imaging data of the patient, (2) therapy session imaging data of the patient, or (3) rigid or deformable registration information between the planning imaging data of the patient and the therapy session imaging data of the patient.

18. The computer-implemented method of claim 1, comprising determining at least one of:
dose data;
dose volume histogram (DVH) data;
fractional biologically effective dose data;
tumor control probability (TCP) data;
normal tissue complication probability (NTCP) data; and
region of interest volume data.

19. The computer-implemented method of claim 1, comprising:
determining predictive trend information of at least one predictive trend including at least one of:
a dose data trend;
a fractional biologically effective dose data trend;
a tumor control probability (TCP) data trend;
a normal tissue complication probability (NTCP) data trend;
a dose volume histogram (DVH) trend;
a dose isocontours trend; and
a region of interest trend.

20. The computer-implemented method of claim 19, comprising using the predictive trend information with the initial or adapted patient care plan to predict at least one subsequent course of radiation therapy.

21. The computer-implemented method of claim 19, comprising using the predictive trend information with the initial or adapted treatment plan to trigger a notification of at least one of a user error, a treatment error, or a treatment deviation.

22. The computer-implemented method of claim 1, wherein managing the workflow comprises monitoring a quality assurance indication about a delivery of a predetermined radiation dose to a patient in accordance with the initial patient care plan relative to any adaptation to the initial patient care plan.

23. The computer-implemented method of claim 1, wherein a radiation therapy session includes one or more fractions of a course of radiation therapy.

* * * * *